United States Patent [19]

Sevick-Muraca et al.

[11] Patent Number: 5,865,754
[45] Date of Patent: Feb. 2, 1999

[54] FLUORESCENCE IMAGING SYSTEM AND METHOD

[75] Inventors: Eva M. Sevick-Muraca, Lafayette, Ind.; Dilip Y. Paithankar, Westboro, Mass.

[73] Assignee: Purdue Research Foundation Office of Technology Transfer, West Lafayette, Ind.

[21] Appl. No.: 702,060

[22] Filed: Aug. 23, 1996

Related U.S. Application Data

[60] Provisional application No. 60/002,746, Aug. 24, 1995.
[51] Int. Cl.$^6$ ........................................ A61B 5/00
[52] U.S. Cl. .......................... 600/476; 356/317; 356/318; 600/473
[58] Field of Search ................................. 128/633, 664, 128/665; 600/310, 473, 476; 356/317, 318

[56] References Cited

U.S. PATENT DOCUMENTS

| 4,541,438 | 9/1985 | Parker et al. ........................... 128/664 |
| 5,022,757 | 6/1991 | Modell . |
| 5,142,372 | 8/1992 | Alfano et al. . |
| 5,213,105 | 5/1993 | Gratton et al. . |
| 5,340,991 | 8/1994 | Fransen et al. . |
| 5,353,799 | 10/1994 | Chance . |
| 5,413,098 | 5/1995 | Benaron ................................. 128/633 |
| 5,421,337 | 6/1995 | Richards-Kortum et al. . |
| 5,421,339 | 6/1995 | Ramanujam et al. ................... 128/665 |

(List continued on next page.)

FOREIGN PATENT DOCUMENTS 2-268256  1/1990  Japan .

OTHER PUBLICATIONS

E.M. Sevick et al., "Localization of absorbers in Scattering Media by use of frequency–domain measurements of time–dependent photon migration", *Applied Optics* vol. 33, No. 16, Jun. 1994 pp. 3562–3570.

Richard Haskel et al., "Boundary conditions for the diffusion equation in radiative transfer", J. Opt. Soc. Am. ,A. vol. 11, No. 10, Oct. 1994, pp. 2727–2741.

R.L. Sheridan et al., "Burn depth estimation by use of indocyanine green fluorescence: Initial human trial", Journal of Burn Care & Rehabilitation, vol. 16 No. 4, pp.1–5.

M.A. O'Leary et al., "Flourescence lifetime imaging in turbid media", Optics Letters, vol. 21 No. 2, Jan. 1996, pp. 158–160.

(List continued on next page.)

*Primary Examiner*—George Manuel
*Assistant Examiner*—Eleni Mantis Mercader
*Attorney, Agent, or Firm*—Woodard, Enhardt, Naughton Moriarty & McNett

[57]  ABSTRACT

A system and method non-invasive biomedical optical imaging and spectroscopy with low-level light is described. The technique consists of a modulated light source (120) coupled to tissue (100) of a patient to introduce excitation light. Fluorescent light emitted in response to the excitation light is detected with sensor (148). The AC intensity and phase of the excitation and detected fluorescent light is provided to a processor (160) operatively coupled to sensor (148). Processor (160) employs the measured re-emission kinetics of excitation and fluorescent light to "map" the spatial variation of one or more fluorescence characteristics of the tissue (100). The fluorescence characteristic may be provided by exogenous contract agents, endogenous fluorophores, or both. The variation is determined by solving frequency domain diffusion equations at a number of designated points in the tissue as part of a recursive estimation algorithm. Processor (160) generates an imaging signal in accordance with the spatial variation of the fluorescence characteristic for provision to an output device (164). The output device (164) displays an image corresponding spatial variation of the fluorescence characteristic which corresponds to tissue (100) to aid in the detection and diagnosis of disease.

47 Claims, 15 Drawing Sheets

U.S. PATENT DOCUMENTS

| | | | |
|---|---|---|---|
| 5,441,054 | 8/1995 | Tsuchiva | 128/665 |
| 5,452,723 | 9/1995 | Wu et al. | |
| 5,507,287 | 4/1996 | Palcic et al. | 128/633 |
| 5,579,773 | 12/1996 | Vo-Dinh et al. | 128/665 |
| 5,590,660 | 1/1997 | MacAulay | 128/664 |
| 5,647,368 | 7/1997 | Zeng et al. | 128/665 |

OTHER PUBLICATIONS

Huabei Jiang et al., "Optics image reconstruction using frequency–domain data: simulations and experiments", J. Opt. Soc. Am., vol. 13, No. 2, Feb. 1996, pp. 253–266.

Alwin Dienle et al., "Spatially resolved absolute diffuse refletance measurements for noninvasive determination of the optical scattering and absorption coefficients of biological tissue", Applied Optics, vol. 35, No. 13 May 1996, pp. 2304–2314.

X.D. Li et al., "Fluorescent diffuse photon density waves in homogeneous and heterogeneous turbid media: analytic solutions and applications", Applied Optics, vol. 35, No. 19, Jul. 1996, pp. 3746–3758.

Michael Patterson et al., "Applications of time–resolved light scattering measurements to photodynamic therapy dosimetry", Applied Optics 1203–1208.

Michael Patterson et al., "Diffusion equation representation of photon migration in tissue".

Eva Sevick–Muraca et al., "Origin of phosphorescence signals reemitted from tissues", Optics Letters, vol. 19, No. 23, Dec. 1994, pp. 1928–1930.

Christina Hutchinson et al., "Fluorescence lifetime–based sensing in tissues: a computational study", Biophysical Journal, vol. 68, Apr. 1995 pp. 1574–1584.

B.W. Pogue et al., Initial assessment of a simple system for frequency domain diffuse optical tomography, Phys. Med. Biol. 40, (1995) 1709–1729.

Stefan Anderson–Engels et al., "Laser–induced fluorescence in malignant and normal tissue of rats injected with benzoporphyrin derivative", Photochemistry and Photobiology, vol. 57, No. 6, pp. 978–983, 1993.

Jun Wu et al., "Three–dimensional imagin of objects embedded in turbid media with fluorescence and raman spectroscopy", Applied Optics, vol. 34, No. 18, Jun. 1995 pp. 3425–3430.

Scott R. Fulton, et al., "Time–resolved laser–indused fluorescence spectroscopy for enhanced demarcation of human atherosclerotic plaques", Journal of Photochemistry and Photobiology, (1990) pp. 363–369.

Seth Fraden et al., "Multiple light scattering from concentrated, interacting suspensions", Physical Review Letters, vol. 65, No.4, pp. 512–515.

K.M. Yoo et al., "Imaging objects hidden in scattering media using a fluorescence–absorption technique", Optics Letters, vol. 16, No. 16, 1991, pp. 1252–1254.

R.C. Straight et al., "Application of Charge–coupled device technology for measurement of laser light and fluorescence distribution in tumors for photodynamic therapy", Photochemistry and Photobiology, vol. 53, No. 6, pp. 787–796.

E. M. Sevick, et al., "Frequency domain imaging of absorbers obscured by scattering" J. Photochem, Photobiol. B: Biol., 16 (1992) pp. 169–185.

Wai S. Poon et al., "Laser–induced Fluorescence: Experimental intraoperative delineation of tumor resection margins", J. Neurosung, vol. 76, Apr. 1992, pp. 679–686.

Brian C. Wilson et al., "Time–dependent optical spectroscopy and imaging for biomedical applications", Proceedings of the IEEE, vol. 80, No. 6, Jun. 1992 pp. 918–930.

A. Knuittel et al., "Acoust–optic scanning and interfering photon density waves for precise localization of an absorbing (or fluorescence body in a turbid medium", Rev. Sci. Instrum, vol. 64, No. 3, Mar. 1993, pp. 638–644.

R. Cubeddu et al., "Time–gated Fluorescence imaging for the diagnosis of tumors in a murine model", Photochemistry and Photobiology, vol. 57, No. 3, pp. 480–485.

Randall Barbour et al., "A perturbation approach for optical diffusion tomography using continuous–wave and time–resolved data", Medical Optical Tomography, pp. 87–121.

M.A O'Leary et al., "Reradiation and imaging of diffuse photon density waves using fluorescent inhomogeneities", Journal of Luminescence, (1994) pp. 281–286.

Michael S. Patterson et al., "Mathematical model for time–resolved and frequency–domain fluorescence spectroscopy in biological tissues", Applied Optics, vol. 33, No. 10, Apr. 1994, pp. 1963–1974.

David A. Russel et al., "Continuous noninvasive measurement of InVivo pH in conscious mice", Photochemistry and Photobiology, vol. 59, No. 3 (1994) pp. 309–313.

Serge Mordon et al., "In Vivo pH measurement and imaging of tumor tissue using a pH–sensitive fluorescent probe (5, 6–carboxyfluorescein): Instrumental and Experimental studies", Photochemistry and Photobiology, vol. 60, No. 3, pp. 274–279.

Jun Wu et al., "Time–resolved multichannel imaging of fluorescent objects embedded in turbid media", Optic Letters, vol. 20, No. 5, Mar. 1995 pp. 489–491.

FLUORESCENCE IMAGING SYSTEM AND METHOD

This application claims benefit of provisional application Ser. No. 60/002,746 filed, Aug. 24, 1995.

BACKGROUND OF THE INVENTION

The present invention relates to spectroscopic imaging of heterogeneous light scattering media, and more particularly, but not exclusively, relates to in vivo imaging of biologic tissue by mapping a fluorescence characteristic of the tissue through the detection of light emitted in response to excitation light from a time-varying light source.

The early detection of disease promises a greater efficacy for therapeutic intervention. In recent years, non-invasive techniques have been developed which have improved the ability to provide a reliable and early diagnosis of various afflictions by detecting biochemical changes in the tissue of a patient. For example, Magnetic Resonance Imaging (MRI) has successfully monitored the relaxation of spin states of paramagnetic nuclei in order to provide biomedical imaging and biochemical spectroscopy of tissues. Unfortunately, the complexity and expense of MRI diagnostics limit its availability—especially as a means of routine monitoring for disease.

Another powerful analytical technique with an increasing number of applications in the biological sciences is fluorescence spectroscopy. These applications include biomedical diagnostics, genetic sequencing, and flow cytometry. To date, there are several industrial and academic institutions developing fluorescent and phosphorescent compounds for observing pertinent metabolites and environmental conditions, such as $Ca^{++}$, pH, glucose, $pO_2$, and $pCO_2$. With the development of dyes and photodynamic fluorescent agents which excite and re-emit in the near-infrared red (NIR) wavelength regime, non-invasive detection of diseased tissues located deep within tissues may also be possible since red excitation and re-emission light can travel significant distances to and from the tissue-air interface (See Wilson et al., *Time-Dependent Optical Spectroscopy and Imaging for Biomedical Applications,* 80 Proceedings IEEE pp. 918–30 (1992)).

As exemplified by U.S. Pat. Nos. 5,421,337 to Richards-Kortum et al. and 5,452,723 to Wu et al., several investigators have suggested various procedures to differentiate diseased and normal tissues based on fluorescence emissions through non-invasive external measurements or minimally invasive endoscopic measuring techniques. Unfortunately, these procedures generally fail to provide a viable spatial imaging procedure. One reason imaging based on fluorescence has remained elusive is that meaningful relational measurements of fluorescence characteristics from a random, multiply scattering media, such as tissue, are difficult to obtain. For example, fluorescent intensity, which is a function of the fluorescent compound (or fluorophore) concentration or "uptake," is one possible candidate for imaging; however, when this property is used in an optically dense medium, such as a particulate (cell) suspension, powder, or tissue, the local scattering and absorption properties confound measured fluorescent intensities.

Besides intensity, other properties of selected fluorophores such as fluorescent quantum efficiency and lifetime are also sensitive to the local biochemical environment. As used herein, "fluorescent quantum efficiency" means the fractional number of fluorescent photons re-emitted for each excitation photon absorbed or the fraction of decay events which result in emission of a fluorescent photon. "Fluorescent lifetime," as used herein, is defined as the mean survival time of the activated fluorophore or the mean time between the absorption of an excitation photon and re-emission of a fluorescent photon. Like intensity, measurement of these fluorescence characteristics is often limited to well-defined in vitro applications in the research laboratory or in flow cytometry where issues such as scattering, absorption, and changing fluorophore concentrations can be controlled or measured. Moreover, these limitations generally preclude meaningful fluorescence-based imaging of hidden tissue heterogeneities, such as tumors or other diseased tissue regions which cannot be detected by visual inspection.

Thus, a need remains for a technique to non-invasively image multiply scattering tissue based on one or more fluorescence characteristics which does not require extensive information about intrinsic optical properties of the tissue, and takes advantage of the contrast capability offered by fluorescence yield and lifetime characteristics to aide in the identification of tissue heterogeneities. The present invention satisfies this need.

SUMMARY OF THE INVENTION

The invention relates to spectroscopic imaging of heterogeneous, light scattering materials. Several aspects of the invention are novel, non-obvious, and provide various advantages. While the actual nature of the invention covered herein can only be determined with reference to the claims appended hereto, certain features which are characteristic of the present invention are described briefly as follows.

One feature of the present invention is a technique for imaging a heterogeneous light scattering material. This process includes exposing the surface of a material to light from a light source and detecting an emission in response. A spatial variation of a fluorescence characteristic of the material is determined as a function of the emission with a processor. The spatial variation may be characterized by a set of values representative of the fluorescence characteristic as a function of position. An image is generated in accordance with the spatial variation which corresponds to the heterogeneous composition of the material. This technique may be applied in vivo to biologic tissue using external or endoscopic instrumentation to detect heterogeneities indicative of disease. The technique may include the introduction of a fluorescent contrast agent into the material. The fluorescence characteristic detected may be fluorescence lifetime, fluorescence quantum efficiency, a fluorophore absorption coefficient, fluorescent yield (a function of fluorescent quantum efficiency and fluorophore absorption), or another fluorescence characteristic known to those skilled in the art.

In another feature of the present invention, the spatial variation of a light scattering material with a heterogeneous composition is determined by establishing an estimate of the optical property or fluorescence characteristic variation, determining a calculated emission from the material as a function of the estimate, and comparing the calculated emission to a detected emission to determine a corresponding error. The estimation of the variation is modified, the calculated emission re-determined with this modified estimate, and the comparison repeated until the error reaches a desired minimum. An image of the material is generated from the modified estimate which corresponds to the heterogeneous composition.

Accordingly, it is one object of the present invention to map a fluorescent property of a light scattering material which varies with the heterogeneous composition of the material to generate a corresponding image.

It is another object of the present invention to provide a spectroscopic technique for non-invasively monitoring fluorescent properties of hidden tissue volumes in a living organism and to monitor selected metabolites of an organism in vivo.

Yet another object is to provide a fluorescence imaging system and process to identify diseased tissue using endogenous or exogenous fluorophores as a contrast agent. This contrast may be provided by a concentration, lifetime, or quantum efficiency difference between normal and diseased tissues.

It is still another object of the present invention to provide an imaging technique and algorithm which is based on contrast of an optical property that is independent of local fluorophore concentration.

Further objects, features, aspects, and advantages of the present invention will become apparent from the drawings and description contained herein.

DESCRIPTION OF PREFERRED EMBODIMENTS

Figure 1:
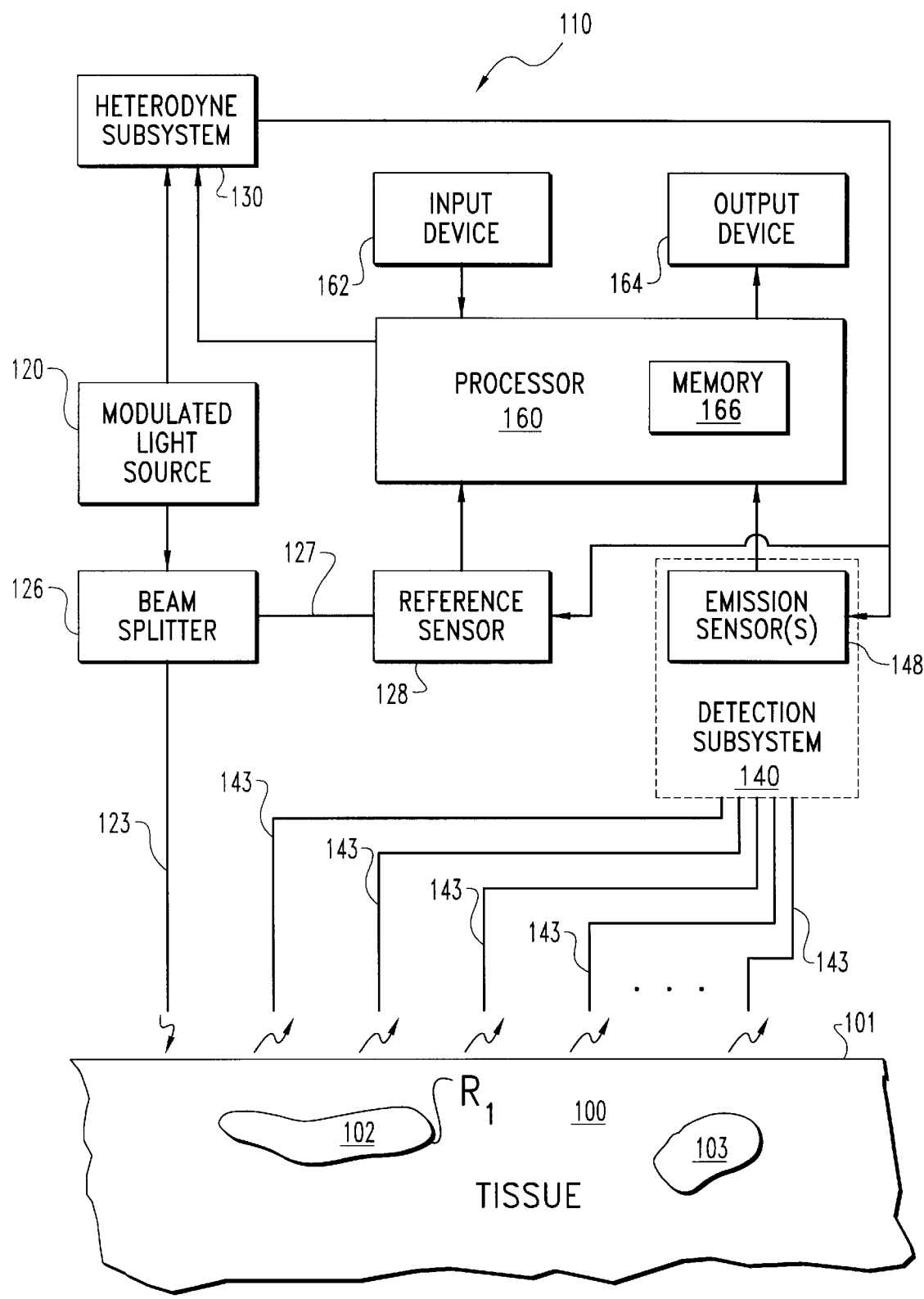
FIG. 1 is a schematic illustration of a system of one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any alterations and further modifications in the described device, and any further applications of the principles of the invention as described herein are contemplated as would normally occur to one skilled in the art to which the invention relates.

FIG. 1 depicts system 110 of the present invention for fluorescent imaging of tissue 100. Tissue 100 has surface 101 and a heterogeneous composition as represented by regions 102, 103 underlying surface 101. Heterogeneities 102, 103 are generally not detectable by visual inspection of surface 101.

System 110 includes modulated light source 120 to supply an intensity modulated excitation light of predetermined frequency and wavelength to tissue 100 via optic fiber 123. Preferably, source 120 is a laser diode of conventional design with a modulated output in the 1–500 MHz frequency range and a monochromatic output in the 100 to 1000 nm wavelength range. The specific wavelength is selected to excite a designated fluorophore in tissue 100. Beam splitter 126 may be employed to direct a small portion of the excitation signal to reference sensor 128 for processing purposes.

System 110 also includes detection subsystem 140 which has optic fibers 143 to detect photons emitted from tissue 100 from a number of corresponding detection sites. Subsystem 140 includes one or more emission sensors 148. Detection subsystem 140 also includes an interference filter to obtain a selected emission wavelength corresponding to emission of a designated fluorophore in tissue 100. In one embodiment, subsystem 140 includes a single sensor 148 and the signals from fibers 143 are multiplexed. Preferably, sensors 128, 148 are Photo-multiplier Tubes (PMTs) or photodiodes but other sensor varieties, such as image intensifiers and charge-coupled devices, are also contemplated.

Sensors 128, 148 and source 120 are operatively coupled to heterodyne subsystem 130. Subsystem 130 is configured to obtain information about the phase, AC, and DC intensity of light detected with sensor 128 relative to light detected with the sensor 148 using conventional laser heterodyning techniques. In one embodiment, heterodyne subsystem 130 includes a signal synthesizer phase-locked to the repetition rate of a laser used for source 120. For this embodiment, subsystem 130 includes an amplifier to gain modulate sensors 128, 148 at a harmonic of a laser repetition rate (when a pulsed laser is used) or at the modulation frequency (when a modulated laser diode is used) plus an offset to provide the desired heterodyning. In one variation of this embodiment, an 80 Hz pulsed laser repetition rate is divided down to 10 MHz and input to the synthesizer, and a heterodyning offset of 100 kHz is input to the amplifiers for sensors 128, 148.

Sensors 128, 148 are operatively coupled to processor 160. Processor 160 includes input/control device 162, output device 164, and memory 166. Processor 160 may be an electronic circuit comprised of one or more components. Similarly, processor 160 may be comprised of digital circuitry, analog circuitry, or both. Also, processor 160 may be programmable, an integrated state machine, or a hybrid combination thereof. Preferably, input device 162 is a keyboard or input control of a conventional variety, and output device 164 is a Cathode Ray Tube (CRT) based video display, printer, or other image display system known to those skilled in the art. Memory 166 is preferably of the electronic (e.g. solid state), magnetic, or optical variety of the type readily available for use with electronic controllers or processors. Furthermore, Memory 166 may include an optical disk memory (CD), electromagnetic hard or floppy disk media, or a combination of these.

Figure 2:
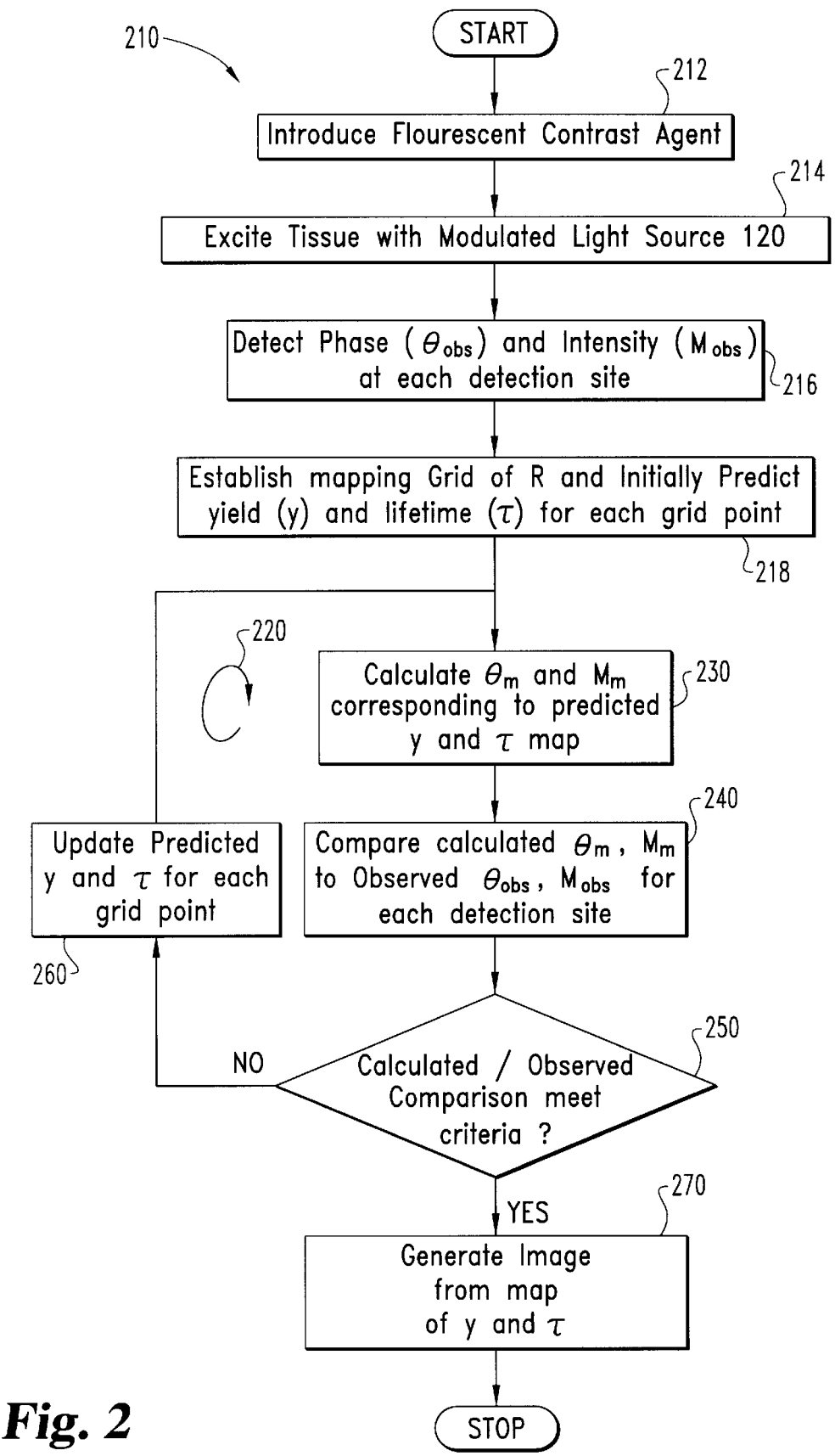
FIG. 2 is a flow chart of a process utilizing the system of FIG. 1.

FIG. 2 depicts one mode of operation of system 110 as process 210. Process 210 includes mapping the spatial variation of fluorescence yield and lifetime with processor 160 and generating an image signal in accordance with the map. Output device 164 is configured to display an image in response to the image signal. Process 210 begins by introducing a fluorescent contrast agent into tissue 100 in stage 212. This agent provides a source of fluorescent emission for detection by subsystem 240. The configuration of the modulated light source 120, heterodyne subsystem 130, and detection subsystem 140 is designed to accommodate the excitation and emission properties of the selected fluorescent agent. In other embodiments, endogenous fluorophores may be alternatively or additionally employed and system 110 adjusted accordingly.

In stage 214, tissue 100 is excited by light source 120 configured according to the selected fluorophore. In stage 216, the phase, $\theta_{obs}$, and log of AC intensity, $M_{obs}$, of the emission at each detection site "i" relative to the excitation light from source 120 are determined at the heterodyne (or offset) frequency. For "Di" number of detection sites, the detected or observed phase and AC intensity are indexed by "i" using the following notation: $(\theta_{obs})_i$ and $(M_{obs})_i$, respectively. Processor 160 stores the relative phase and AC intensity information in memory 166.

In stage 218, a two dimensional grid is established for an area of tissue 100 selected for imaging, and a matrix of grid points is established and indexed by "j". A uniform seed value for the fluorescent yield, $y_j = (\eta \mu_{a_{x \to m}})_j$, and the fluorescent lifetime, $(\tau)_j$, at each grid point j is assigned. These values are an initial homogeneous guess of the yield and lifetime values which are modified in later stages. The term "$\eta$" is the quantum efficiency of the fluorophore which varies with the environment of the surrounding of the fluorophore. The term "$\mu_{a_{x \to m}}$" is the absorption coefficient for the fluorophore and is the product of the extinction coefficient of the fluorophore based on the natural log and the concentration of the fluorophore. As a result, the yield, $y = \eta \mu_{a_{x \to m}}$, is influenced by the surrounding metabolism and the uptake of the fluorophore. The uptake of certain known fluorophores vary with the type and condition of host tissue, providing another fluorescence characteristic useful to detect disease. The contrast provided by these properties is largely independent of fluorophore concentration. The initial estimate of fluorescent yield and lifetime are stored in memory 166 by processor 160 for later use.

After establishing this initial estimate of the fluorescence characteristics of yield, $\eta \mu_{a_{x \to m}}$, and lifetime, $\tau$, processing loop 220 is entered in stage 230. Preferably, the stages of processing loop 220 are executed by processor 160 via preprogrammed software, dedicated hardware, or a combination of both as appropriate. To aid in understanding various mathematical aspects of process 210 and loop 220, the following table of selected variables is listed:

| | |
|---|---|
| c | velocity of light; |
| D(r) | optical diffusion coefficient; |
| Di | number of detection sites; |
| f | modulation frequency; |
| I | identity matrix; |
| i | detection site index; |
| J | Jacobian matrix relating the sensitivity at each grid point, j, to the response at each detection site; |
| j | grid point index; |
| $J_{j,i}$ | individual elements of the Jacobian matrix J; |
| k | source index; |
| M | log of AC intensity of modulated fluorescent light position; |
| m | index to multiple modulation frequencies; |
| n | average index of refraction; |
| r | position (in two or three dimensions); |
| Sk | number of modulated light sources; |
| $S(r,\omega)$ | source term for the modulated light at position r and frequency $\omega$; |
| Greek | |
| $\chi^2$ | merit function representing the least squares error; |
| $\Phi_x(r,\omega)$ | complex number representing photon flux in the frequency domain at position r and frequency $\omega$; |
| $\eta$ | quantum efficiency of fluorescent probe or dye; |
| $\mu_a$ | average absorption coefficient; |
| $\mu_{am}$ | absorption coefficient of the fluorescence light by both the non-fluorescing chromophores and fluorophore; |
| $\mu_{ax}$ | absorption coefficient of the excitation light by both the non-fluorescing chromophores and fluorophore; |
| $\mu_{ax \to c}$ | adsorption coefficient due to non-fluorescing chromophores; |
| $\mu_{ax \to m}$ | adsorption coefficient of excitation light by fluorophores; |
| $\mu'_s$ | effective scatting coefficient; |
| $\theta$ | phase-shift of one modulated light wave to another; |

-continued

| | |
|---|---|
| $\tau$ | lifetime of activated probe or dye at location r; |
| $\omega$ | angular modulation frequency, given by $2\pi f$; |
| Subscripts | |
| obs | observed or experimental data; |
| x | excitation light; and |
| m | fluorescence or emission light |

In stage 230, phase and relative AC intensity at each detection site "i" is calculated as a function of the initial estimates of yield and lifetime for each grid point j. The calculated phase and intensity are represented at each detection site i as $(\theta_m)_i$ and $(M_m)_i$, respectively. The values for $(\theta_m)_i$ and $(M_m)_i$ are determined using the diffusion equation approximation of the radiative transport equation. The diffusion equation approximation describes the spatial and temporal transport of light in tissues or multiply scattering media A coupled frequency domain diffusion equation can be used to predict the excitation and emission fluence rates, $\Phi_x(r,\omega)$ and $\Phi_m(r,\omega)$, respectively, at any location r within the selected grid of tissue 100 via equations (1) and (2):

$$\nabla \cdot [D_x(r) \nabla \Phi_x(r,\omega)] - [\mu_{a_x}(r) + i\,\omega/c_n]\Phi_x(r,\omega) + S_x(r,\omega) = 0 \quad (1)$$

$$\nabla \cdot [D_m(r) \nabla \Phi_m(r,\omega)] - [\mu_{a_m}(r) + i\,\omega/c_n]\Phi_m(r,\omega) + S_m(r,\omega) = 0 \quad (2)$$

The source term for the excitation light $S_x(r,\omega)$ is due to the sinusoidally modulated light at an angular frequency $\omega = 2\pi f$ where f is typically in the MHz frequency range. The first term in both of the diffusion equations (1) and (2) represents the diffusive or "random-walk" transport of light where $D_{x,m}$ is the optical diffusion coefficient of equation (3) as follows:

$$D_{x,m} = [3(\mu_{a_{x,m}} + \mu'_{s_{x,m}})]^{-1} \quad (3)$$

and $\mu_a$ and $\mu'_s$ are the absorption and isotropic scattering coefficients, respectively, for tissue 100, the medium of interest. The optical properties are dependent on the wavelength of light and thus are different for the excitation light from source 120 (subscript x) and fluorescent emission detected with subsystem 140 (subscript m). The total absorption coefficient at the excitation wavelength, $\mu_{a_x}$, is due to contributions from non-fluorescing chromophores as well as from fluorophores responsive to the excitation wavelength. The total absorption coefficient is given by the sum of absorption coefficients due to non-fluorescing chromophores, $\mu_{a_{x \to c}}$, and fluorophores $\mu_{a_{x \to m}}$. Generally it may be assumed that the absorption experienced at the fluorescent wavelength is due primarily to non-fluorescing chromophores. The velocity of light in tissue is $c_n = c/n$ where n is the average index of refraction. The source term for the fluorescent emission is dependent on the excitation light fluence, $\Phi_x(r, \omega)$ and is given by equation (4) as follows:

$$S_m(r,\omega) = \eta \mu_{a_{x \to m}}(r) \Phi_x(r,\omega)[(1 - i\omega\tau(r))/(1 + \omega^2 \tau(r)^2)] \quad (4)$$

This term arises from the Fourier transform of the fluorescence decay term in the time domain following an incident pulse of excitation light where: $\tau$ is the fluorophore lifetime, $\eta$ is the quantum efficiency, and the absorption coefficient, $\mu_{a_{x \to m}}$, is the product of the extinction coefficient based on natural log and the concentration of the fluorophore in the ground state. As previously indicated, the combined product, $\eta \mu_{a_{x \to m}}$, is termed the fluorescent yield, y, and is proportional to the generated fluorescence fluence. Substitution of equation (4) into equation (2) facilitates determination of $\Phi_m$ for each grid point "j." The solution of the diffusion equations (1) and (2) for the two-dimensional area defined by the grid points "j" may be readily extended to three dimensions to estimate spatial variation of one or more fluorescence characteristics in a selected volume with "r" corresponding to position in three dimensions.

Both diffusion equations (1) and (2) are linear complex elliptic equations that can be solved as boundary value problems for the complex quantities $\Phi_x(r,\omega)$ and $\Phi_m(r,\omega)$. This solution employs the method of finite differences to create corresponding finite difference equations. These difference equations are utilized to obtain an approximate solution at each grid point, j. This method of solution is described in other contexts in Fulton et al., *Multigrid Method for Elliptic Problems. A Review*, 114 American Meteorological Society pp.943–59 (May 1986); and B. W. Pogue et al., *Initial Assessment of a Simple System for Frequency Domain Diffuse Optical Tomography*, 40 Physics in Medicine and Biology pp.1709–1729 (1995). One preferred method of performing this solution is with the MUD-PACK routines described in Adams, J. C., *MUDPACK: Multigrid Portable Fortran Software for the Efficient Solution of Linear Elliptic Partial Differential Equations*, 34 App. Math Comp. p.133 (1989). For the solution of the diffusion equations, it is assumed that $\Phi_{m,x}(r,\omega)=0$ on the surface 101 of tissue 100 which is known as the zero fluence boundary condition. It should be recognized that other boundary conditions may be selected and the method of solution varied accordingly.

The diffusion equations (1) and (2) may be solved for a complex number for $\Phi_m$ at each grid point, j. The detected signal at the surface is proportional to the normal component of the gradient of the photon fluence. To approximate the signal at detector site "i" located on surface 101 of tissue 100, the $\Phi_m$ value at an internal grid point closest to the site is selected which follows from the relationship that the normal component of the photon fluence gradient is proportional to $\Phi_m$ just inside surface 101. The calculated phase-lag, $\theta_m$, and the log of AC intensity, $M_m$, at the detection sites "Di" are calculated from the imaginary and real parts of the complex $\Phi_m$ value with respect to the phase and the AC intensity of source 120.

Figure 3:
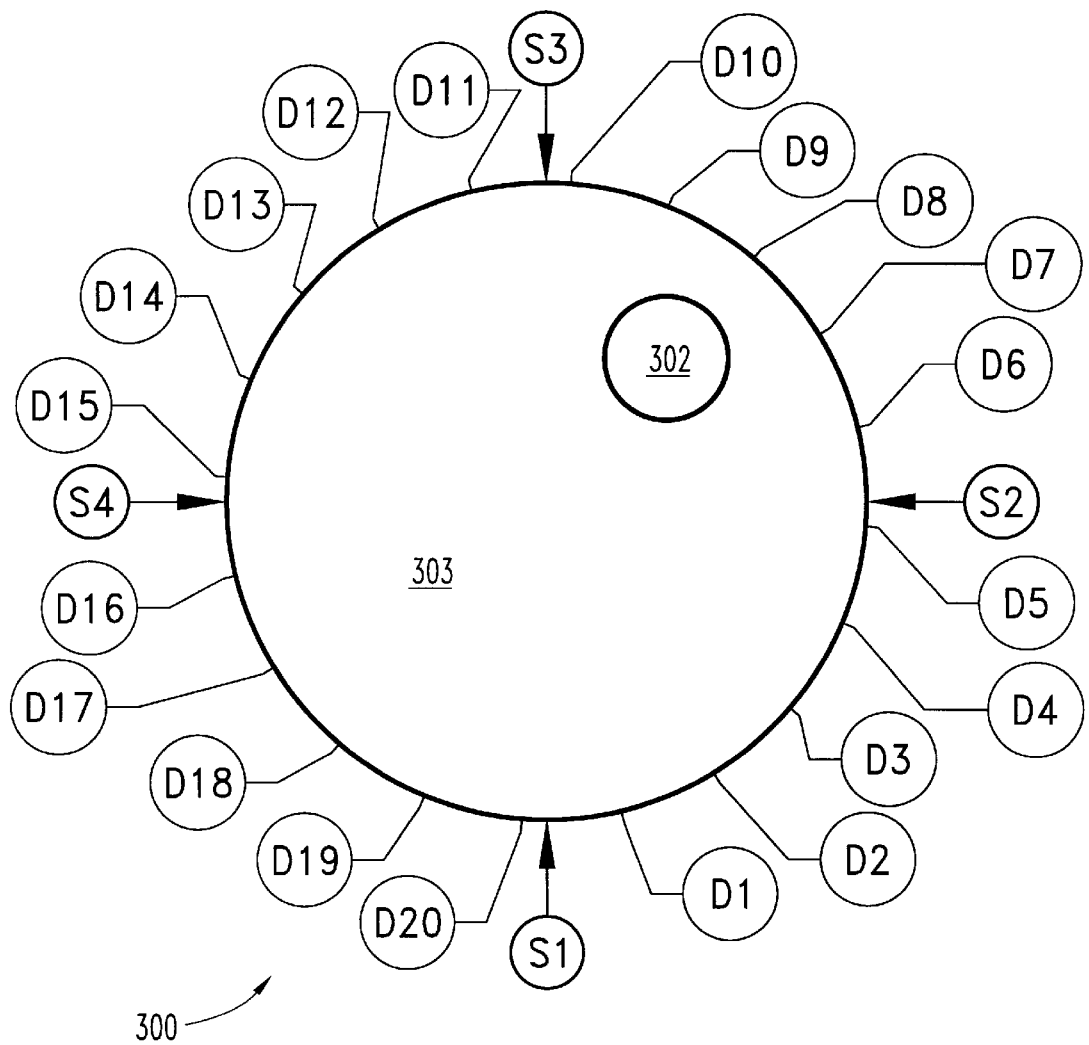
FIG. 3 is a schematic representation of a tissue phantom arrangement used to demonstrate various aspects of the present invention.

The diffusion equations (1) and (2) provide insight into the sensitivity of changing the fluorescent optical properties of tissue 100 on $\theta_m$ and $M_m$ measured at the detector sites i. This insight results from a series of calculations while fixing various parameters of the diffusion equations (1) and (2). These calculations assume circular tissue phantom 300 with an embedded, heterogeneity 302 hidden in phantom background 303 as illustrated in FIG. 3. A two-dimensional grid is established for phantom 300 and may easily be expanded to three dimensions. Under these simulated conditions, a large value is assigned to absorption coefficients for both excitation and fluorescent light at all grid points outside the simulated tissue phantom. The four sources S1–S4 of FIG. 3 (Sk=4) are simulated by assigning an arbitrary complex number at a grid point near the surface closest to each source. The twenty detection sites D1–D20 of FIG. 3 (Di=20) are simulated by using the calculated values determined from $\Phi_m$ at the grid point "j" closest to the detection site. The simulated solutions to diffusion equations (1) and (2) were obtained in two dimensions for a 65×65 grid covering a 100 mm diameter circular tissue phantom 300 with a circular, embedded heterogeneity having a 30 mm diameter and located at the center of the tissue phantom 300 (this location differs slightly from the configuration of heterogeneity 302 of FIG. 3). The simulated measurements of fluorescent phase-shift and AC intensity are reported for 20, equally spaced, circumferentially located detection sites D1–D20. The modulation frequency, f, was set equal to 150 MHz. The optical properties of the heterogeneity and the background are shown in Table 1 as follows:

TABLE 1

| $\mu_{ax\to}$ (mm$^{-1}$) | $\mu_{am}$ (mm$^{-1}$) | $\mu_{sx}$ or $\mu_{sm}$ (mm$^{-1}$) | $\mu_{ax\to c}$ (mm$^{-1}$) | $\eta\mu_{ax\to m}$ background (mm$^{-1}$) | $\tau$ background (ns) | frequency (MHz) |
|---|---|---|---|---|---|---|
| $\mu_{ax\to c} + \mu_{ax\to m}$ | 0.0 | 1.0 | 0.0 | $1.0 \times 10^{-5}$ | 1.0 | 150.0 |

Figure 4:
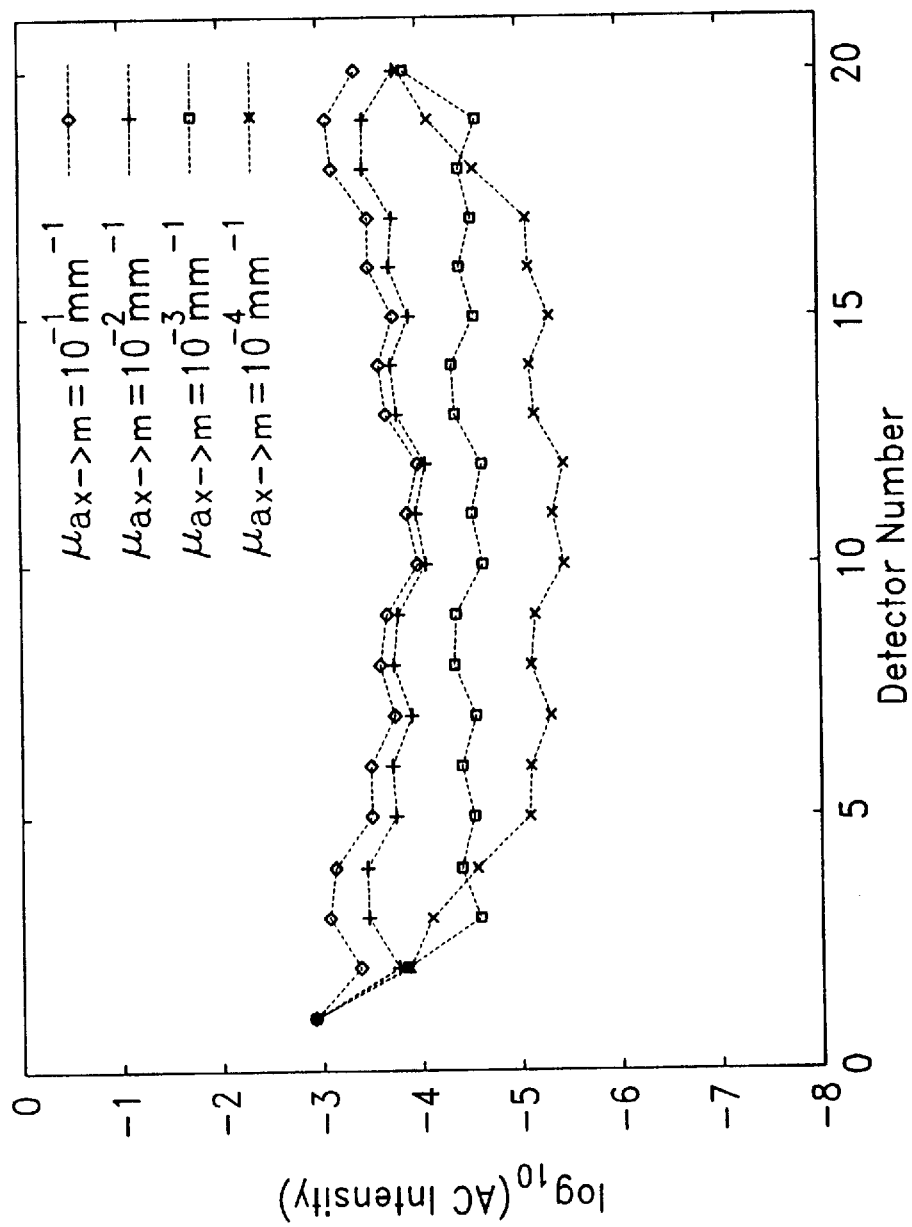
FIGS. 4–7 graphically depict selected properties of equations used in the present invention.
Figure 5:
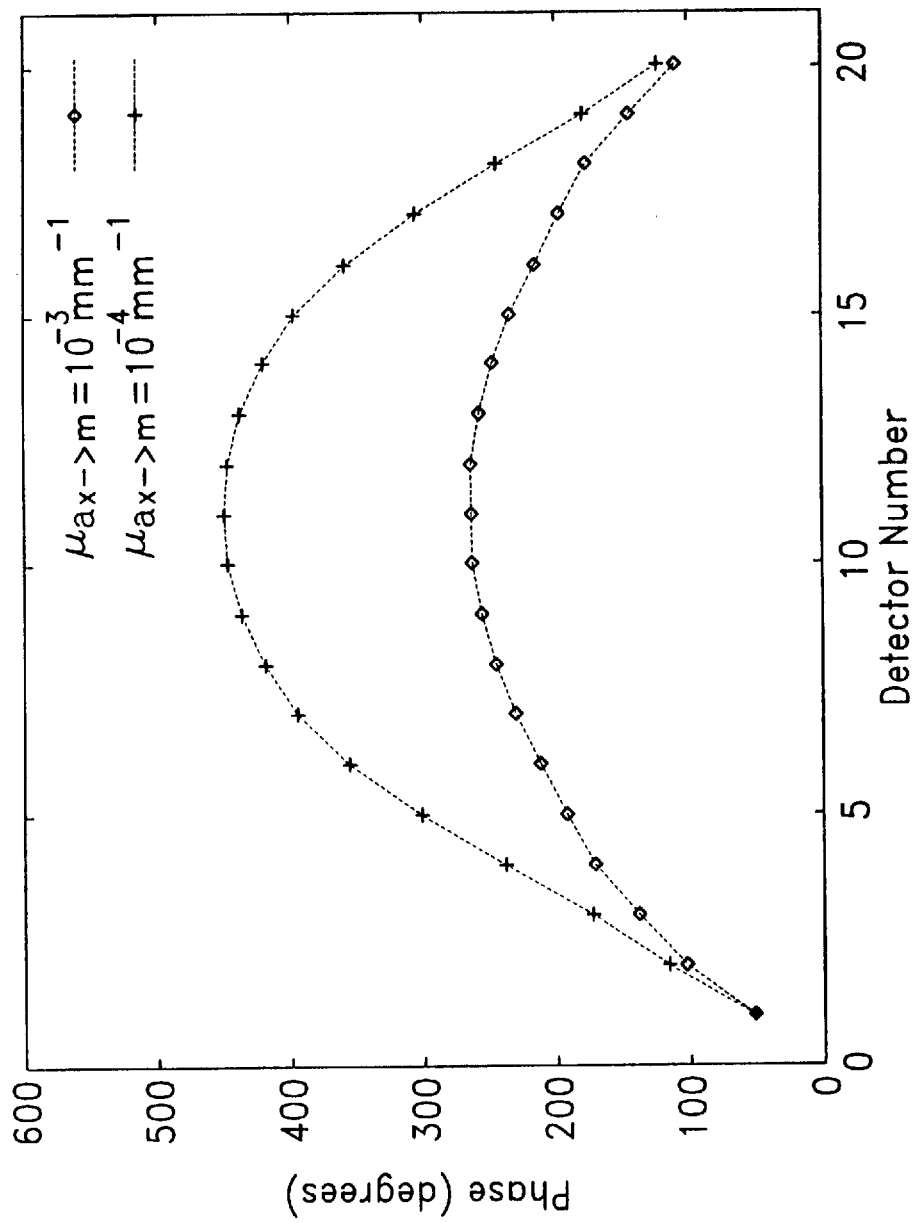

In order to evaluate the influence of $\eta\mu_{a_{x\to m}}$, $\theta_m$ and $M_m$ were computed at each detection site D1–D20 as the value of $\eta\mu_{a_{x\to m}}$ in the heterogeneity increased from $10^{-4}$ mm$^{-1}$ to $10^{-1}$ mm$^{-1}$ and as $\eta\mu_{a_{x\to m}}$ in the background 303 was maintained constant. The lifetime, $\tau$, was set equal to 1 ns for both the object and the background causing contrast due to differences $\eta\mu_{a_{x\to m}}$. The plots of $\theta_m$ and $M_m$ are shown in FIGS. 4 and 5 respectively for one active source S1. As $\eta\mu_{a_{x\to m}}$ of heterogeneity 102 increases to higher values, the AC intensity approaches an upper limit similar to what is expected in dilute non-scattering solutions. FIG. 5 shows how the fluorescent phase-shift, $\theta_m$, decreases as the absorption coefficient due to the fluorophore, $\mu_{a_{x\to m}}$ is decreased 10 to 100 times the background. From these simulations, $M_m$ appears to be directly dependent upon changes in $\eta\mu_{a_{x\to m}}$ of a simulated tissue heterogeneity 102 whereas $\theta_m$ is indirectly dependent on $\eta\mu_{a_{x\to m}}$ due to changes in photon migration.

Figure 6:
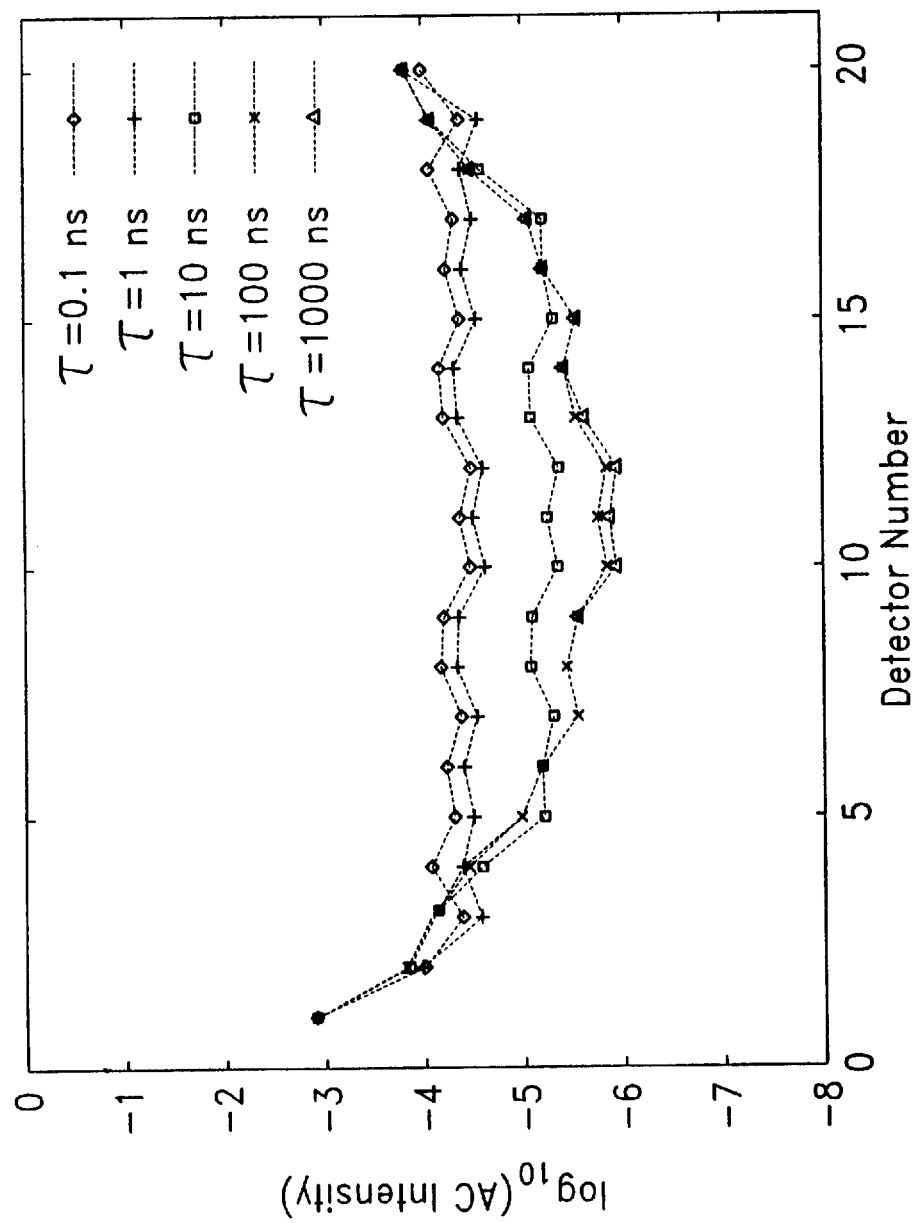
Figure 7:
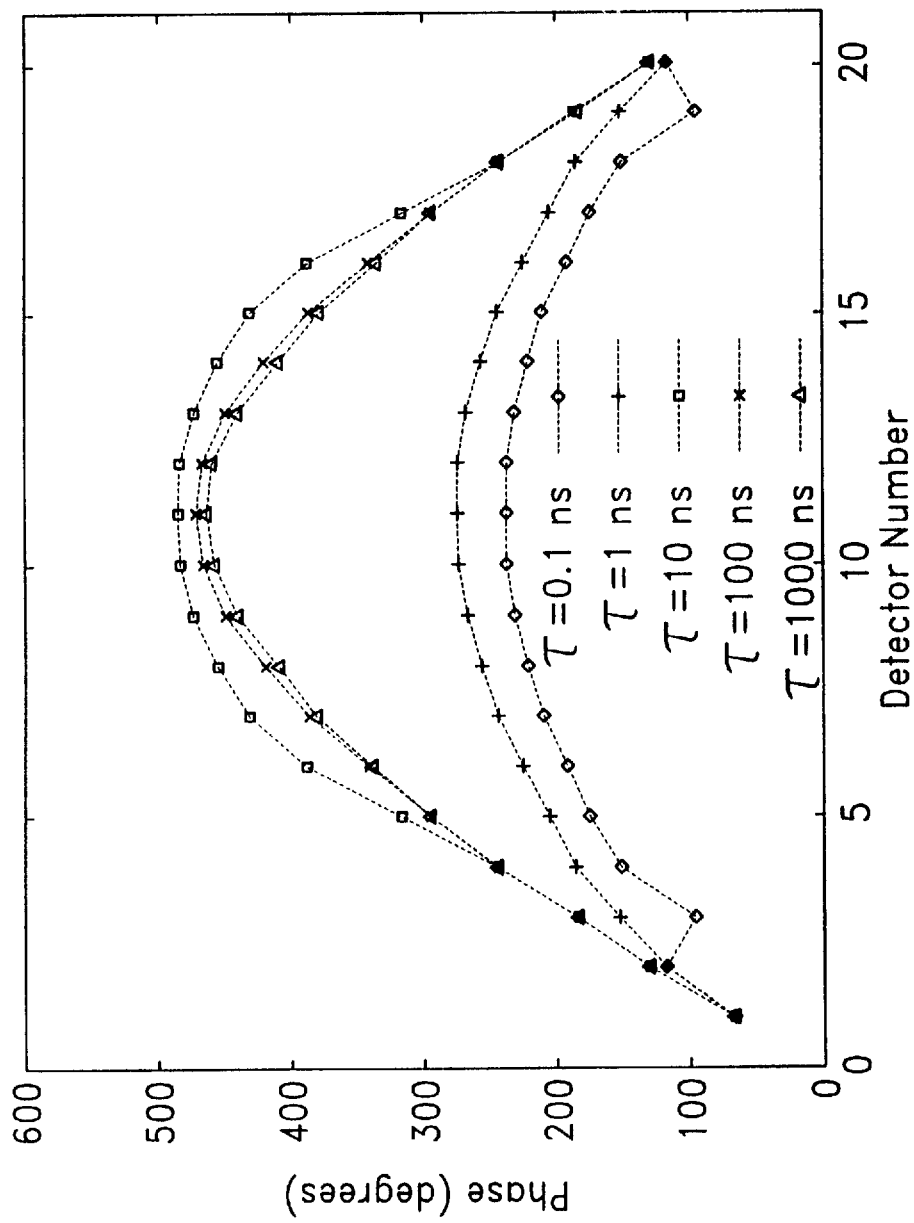

In order to evaluate the influence of $\tau$, $\theta_m$ and $M_m$ were calculated at each detection site D1–D20 as the values of $\tau$ in the heterogeneity varied from $10^{-1}$ ns to $10^3$ ns and the value of $\tau$ in the background was held at 1 ns. The background $\eta\mu_{a_{x\to m}}$ was set to $10^{-5}$ mm$^{-1}$ and $\eta\mu_{a_{x\to m}}$ for the heterogeneity was set to $10^{-3}$ mm$^{-1}$. As shown in FIG. 6, the detected AC intensity increases as $\tau$ decreases. FIG. 7 illustrates the values of the fluorescent phase-shift at each detection site as the lifetime of the heterogeneity is changed from 0.1 ns to 1000 ns. At a given modulation frequency (150 MHz in this calculation), $\theta_m$ first increases, reaches a maximum and then subsequently decreases as $\tau$ is increased from 0.1 ns to 1000 ns. Therefore, both $\theta_m$ and $M_m$ at each detection site D1–D20 appear to be directly influenced by the value of lifetime in the heterogeneity.

Referring back to FIG. 2, in stage 240, the calculated emission phase and intensity, $(\theta_m)_i$ and $(M_m)_i$, are compared to the measured emission phase and intensity, $(\theta_{obs})_i$ and $(M_{obs})_i$, for each detection site "i" to identify a difference or "error" between the measured and calculated values. Because $(\eta\mu_{a_{x\to m}})_j$ impacts $(M_m)_i$, this comparison is posed in the form of the merit function $\chi_\mu^2$ of equation (5) as follows:

$$\chi_\mu^2 = (1/Sk) \sum_{k=1}^{Sk} (1/Di) \sum_{i=1}^{Di} [((M_{obs})_i - (M_m)_i)/\sigma_M]^2 \qquad (5)$$

where $\sigma_M$ is the typical standard deviation of noise in $M_m$, taken to be 0.01; Sk=number of excitation source sites indexed by k; and Di=number of detection sites indexed by i. The goal of the algorithm is to minimize $\chi_\mu^2$ by appropriate updates of $(\eta\mu_{a_{x\to m}})_j$. After an initial update of $(\eta\mu_{a_{x\to m}})_j$ another merit function in terms of $(\tau)_j$ participates in the comparison of stage 240. This merit function, $\chi_\tau^2$, is presented as equation (6) as follows:

$$\chi_\tau^2 = \quad (6)$$

$$(1/Sk)\sum_{k=1}^{Sk}(1/Di)\sum_{i=1}^{Di}[((M_{obs})_i - (M_m)_i)/\sigma_M]^2 + [((\theta_{obs})_i - (\theta_m)_i)/\sigma_\theta]^2$$

where $\sigma_\theta$ is the typical standard deviation of noise in $(\theta_m)_i$, taken to be 1 degree; Sk=number of excitation source sites indexed to k; and Di=number of detection sites indexed to i. Since the lifetime influences both $(\theta_m)_i$ and $(M_m)_i$, the phase and AC intensity are used in equation (6).

After the comparison of stage 240 is performed by calculating the merit functions $\chi_\mu^2$, $\chi_\tau^2$, control flows to conditional 250 to test whether the comparison of the observed values, $(\theta_{obs})_i$ and $(M_{obs})_i$, to the calculated values $(\theta_m)_i$ and $(M_m)_i$ via the merit functions meets a selected convergence criteria. This criteria corresponds to the degree of tolerable error in determining the yield and lifetime values. For one embodiment, convergence is achieved when any of the following three quantities, (i) $\chi^2$, (ii) change in $\chi^2$ in successive iterations of loop 220, (ii) relative change in $\chi^2$ in successive iterations of loop 220 is less than a predetermined threshold value of $1.0\times 10^{-2}$. In other embodiments a different comparison calculation and associated conditional may be employed as would occur to one skilled in the art. If conditional 250 is satisfied, control flows to stage 270 and loop 220 is exited; however, if the criteria is not satisfied, execution of loop 220 continues in stage 260.

In stage 260, the yield, $(y)_j = (\eta\mu_{a_{x\to m}})_j$, and lifetime, $(\tau)_j$, for each grid point j is updated so that these values may reach the minimum error corresponding to the comparison stage 240 and conditional 250 test. In order to update these values, Jacobian matrices are used which describe the sensitivity of the response at each detection position i to changes in $(y)_j = (\eta\mu_{a_{x\to m}})_j$, and lifetime, $(\tau)_j$, at each grid point, j. Three Jacobian matrices are employed: $\bar{\bar{J}}e(M, \eta\mu_{a_{x\to m}})$; $\bar{\bar{J}}e(M,\tau)$; and $\bar{\bar{J}}(\theta, \tau)$. The elements Ji,j of these Jacobian matricies are given by $Ji,j=[\partial M_i/(\partial(\eta\mu_{a_{x\to m}})_j]$; $Ji,j = [\partial M_i/\partial\tau_j]$; and $Ji,j = [\partial\theta/\partial\tau_j]$, respectively. These elements may be calculated by solving the diffusion (1) and (2) four times for each grid point, j to obtain $M_{m,i}$ and $\theta_{m,i}$ calculated with $(\tau)_j$ and $(\tau+\delta\tau)_j$ and with $(\eta\mu_{a_{x\to m}})_j$ and $(\eta\mu_{a_{x\to m}}+\delta\eta\mu_{a_{x\to m}})_j$. From least squares minimization, the update to yield and lifetime is calculated. In one preferred embodiment, this updating algorithm is adapted from an algorithm used to reconstruct images obtained by electrical impedance tomography like the algorithm suggested by Yorkey, et al., *Comparing reconstruction Algorithms for Electrical Impedance Tomography*, 34 Transactions in Biomedical Engineering pp. 843–52(1987). The Jacobian Matrices are used to solve for update vectors, $[\overline{\Delta\eta\mu_{a_{x\to m}}}]$ and $[\overline{\Delta\tau}]$, to estimated yield and lifetime vectors, $[\overline{\eta\mu_{a_{x\to m}}}]$ and $[\overline{\tau}]$, respectively. These vectors are of a dimension corresponding to the number of grid points. At each iteration through loop 220, the following Jacobian equations (7) and (8) are solved to determine the update for the estimated yield and lifetime vectors:

$$\left[\frac{\bar{\bar{J}}(M,\eta\mu_{a_{x\to m}})^T\bar{\bar{J}}(M,\eta\mu_{a_{x\to m}})}{\sigma_M^2} + \lambda_1\bar{\bar{I}}\right][\overline{\Delta\eta\mu_{a_{x\to m}}}] = \quad (7)$$

$$\left[\frac{\bar{\bar{J}}(M,\eta\mu_{a_{x\to m}})^T}{\sigma_M^2}(\overline{M_{m_{obs}}} - \overline{M_m})\right]$$

$$\left[\frac{\bar{\bar{J}}(M,\tau)^T\bar{\bar{J}}(M,\tau)}{\sigma_M^2} + \frac{\bar{\bar{J}}(\theta,\tau)^T\bar{\bar{J}}(\theta,\tau)}{\sigma_\theta^2} + \lambda_2\bar{\bar{I}}\right][\overline{\Delta\tau}] = \quad (8)$$

$$\left[\frac{\bar{\bar{J}}(M,\tau)^T}{\sigma_M^2}(\overline{M_{m_{obs}}} - \overline{M_m}) + \frac{\bar{\bar{J}}(\theta,\tau)^T}{\sigma_\theta^2}(\overline{\theta_{m_{obs}}} - \overline{\theta_m})\right]$$

$\overline{M_{m_{obs}}}$ and $\overline{M_m}$ are the observed and calculated vectors of the log of AC intensity at each of the i detection sites, respectively. $\overline{\theta_{m_{obs}}}$ and $\overline{\theta_m}$ are the observed and calculated vectors of the phase lag at each of the i detection sites, respectively. Due to the ill-conditioned nature of the Jacobian matrices, the terms $\lambda_1 I$ or $\lambda_2 I$ are added as part of a Marquardt minimization scheme where I is an identity matrix. The parameters $\lambda_1$ or $\lambda_2$ are adjusted via a Maquardt-Levenberg type algorithm of the type disclosed in Press et al., *Numerical Recipes: The Art of Scientific Computing*, (Cambridge University Press, 1992). Conventional numerical methods are employed to solve the simultaneous linear algebraic equations resulting from the Jacobian matrix equations (7) and (8). The Jacobian matrices are re-calculated at each iteration through loop 220. It has been found that equations (7) and (8) provide a way to select appropriate changes to the yield and lifetime estimates; however, other numerical approaches to recursively iterate to acceptable estimates as would occur to one skilled in the art are also contemplated. Once the update is complete, control returns to stage 230.

If the convergence criteria is satisfied in conditional 250, then estimation of yield and lifetime for the grid points has reached an acceptable minimum and control flows to stage 270. In stage 270 an image signal is generated by processor 160 from the spatial variation of the yield and/or lifetime fluorescence characteristics. This image signal is sent to output device 164 which displays an image in response. Because the fluorescence characteristics of yield and lifetime typically vary with the biologic environment of the fluorophore, this image is generally indicative of tissue variation and offers the capability to detect heterogeneities 102, 103.. For example, laser diodes capable of supplying Near infrared (NIR) light that can penetrate tissue several centimeters, and fluorescent contrast agents responsive to NIR light may be used to provide a viable imaging system. In one embodiment, this system is adapted for use with an endoscope.

Besides yield and lifetime, the spatial variation of other fluorescence characteristics useful to distinguish diseased tissues may be mapped using the diffusion equations (1) and (2). Such alternative fluorescence characteristics include, but are not limited to, quantum efficiency $\eta$ and/or fluorescent absorption coefficient $\mu_{a_{x\to m}}$ determined as separate properties independent of the yield product.

In another embodiment of the present invention, the photon fluence equation and Jacobian estimation process is adapted to determine a map of a designated fluorophore uptake concentration. For this embodiment, a first map of chromophore adsorption coefficients $\mu_{a_{x\to c}}$ and scattering coefficients $\mu'_s$ are determined in the absence of the designated fluorophore by estimating the chromophore adsorption coefficient $\mu_{a_{x\to c}}$ and scattering coefficient $\mu'_s$ at each grid point j in place of the yield and lifetime estimates. Diffusion equation (1) for $\Phi_x(r,\omega)$ may be used in conjunction with modified Jacobian equations (7) and (8) to create this first map. The modification substitutes the chromophore adsorption and scattering coefficients in place of the yield and after adaptation to accommodate these new characteristics as follows:

$$\left[\frac{\bar{\bar{J}}(M_x,\mu_{a_{x\rightarrow c}})^T \bar{\bar{J}}(M_x,\mu_{a_{x\rightarrow c}})}{\sigma_M^2} + \right. \quad (9)$$

$$\left. \frac{\bar{\bar{J}}(\theta_x,\mu_{a_{x\rightarrow c}})^T \bar{\bar{J}}(\theta_x,\mu_{a_{x\rightarrow c}})}{\sigma_\theta^2} + \lambda_2 \bar{\bar{I}}\right][\overline{\Delta\mu_{a_{x\rightarrow c}}}] =$$

$$\left[\frac{\bar{\bar{J}}(M_x,\mu_{a_{x\rightarrow c}})^T}{\sigma_M^2}(\overline{M}_{x_{obs}} - \overline{M}_x) + \frac{\bar{\bar{J}}(\theta_x,\mu_{a_{x\rightarrow c}})^T}{\sigma_\theta^2}(\overline{\theta}_{x_{obs}} - \overline{\theta}_x)\right]$$

and $$\left[\frac{\bar{\bar{J}}(M_x,\mu_s)^T \bar{\bar{J}}(M_x,\mu_s)}{\sigma_M^2} + \frac{\bar{\bar{J}}(\theta_x,\mu_s)^T \bar{\bar{J}}(\theta_x,\mu_s)}{\sigma_\theta^2} + \lambda_2 \bar{\bar{I}}\right][\overline{\Delta\mu_s}] = \quad (10)$$

$$\left[\frac{\bar{\bar{J}}(M_x,\mu_s)^T}{\sigma_M^2}(\overline{M}_{x_{obs}} - \overline{M}_x) + \frac{\bar{\bar{J}}(\theta_x,\mu_s)^T}{\sigma_\theta^2}(\overline{\theta}_{x_{obs}} - \overline{\theta}_x)\right]$$

$$\frac{\partial M_{x_i}}{\partial(\mu_{a_{x\rightarrow c}})_j}, j_{i,j} = \frac{\partial M_{x_i}}{\partial \mu_{sj}}, j_{i,j} = \frac{\partial \theta_{x_i}}{\partial(\mu_s)_j} \text{ and } j_{i,j} = \frac{\partial \theta_{x_i}}{\partial(\mu_{a_{x\rightarrow c}})_j}$$

$$\chi^2 = \frac{1}{n_s}\sum_{k=1}^{n_s}\frac{1}{n_d}\sum_{i=1}^{n_d}\left(\frac{M_{x_{obs,i}} - M_{x_i}}{\sigma_M}\right)^2 + \left(\frac{\theta_{x_{obs,i}} - \theta_{x_i}}{\sigma_\theta}\right)^2 \quad (11)$$

where $n_s$=Sk and $n_d$=Di.

After generating the first map, the designated fluorescent contrast agent is introduced, and the total adsorption coefficient $\mu_{a_x}$ is determined by substituting $\mu_{a_x}$ in place of $\mu_{a_{x\rightarrow c}}$ in equations (9)–(11) to obtain a second map of the total adsorption coefficient. Noting that $\mu_{a_x}=\mu_{a_{x\rightarrow m}}+\mu_{a_{x\rightarrow c}}$, and that the uptake of the fluorescing contrast agent is directly proportional to $\mu_{a_{x\rightarrow m}}$, uptake concentration may be mapped by determining a difference between the adsorption coefficient variations for the first and second maps. This "difference map" may then be used to generate an image corresponding to the uptake concentration.

Another alternative embodiment measures the emission responsive to each of a number of light source modulation frequencies f. The total number of different frequencies employed is designated Mf. To obtain this additional data, an iteration of loop 220 is performed for each frequency f indexed to m. The number of sources, Sk and detection sites Di are indexed to k and i, respectively. This additional data may be used to enhance imaging results obtained with system 110 or to permit reduction of the number of detection sites or excitation source sites in the evaluation. A representative merit function corresponding to this additional data is given in equation (12) as follows:

$$\chi_t^2 = (1/Mf)\sum_{m=1}^{Mf}(1/Sk)\sum_{k=1}^{Sk}(1/Di)\sum_{i=1}^{Di}[((M_{obs})_i - \quad (12)$$

$$(M_m)_i)/\sigma_M]^2 + [((\theta_{obs})_i - (\theta_m)_i)/\sigma_\theta]^2$$

Besides fluorescence yield and lifetime, the multi-frequency method can be employed to map other optical characteristics of interest. Besides a sinusoidally modulated light source, the present invention may be adapted to operate with a pulsed or other time-varying excitation light source in alternative embodiments.

Figure 15:
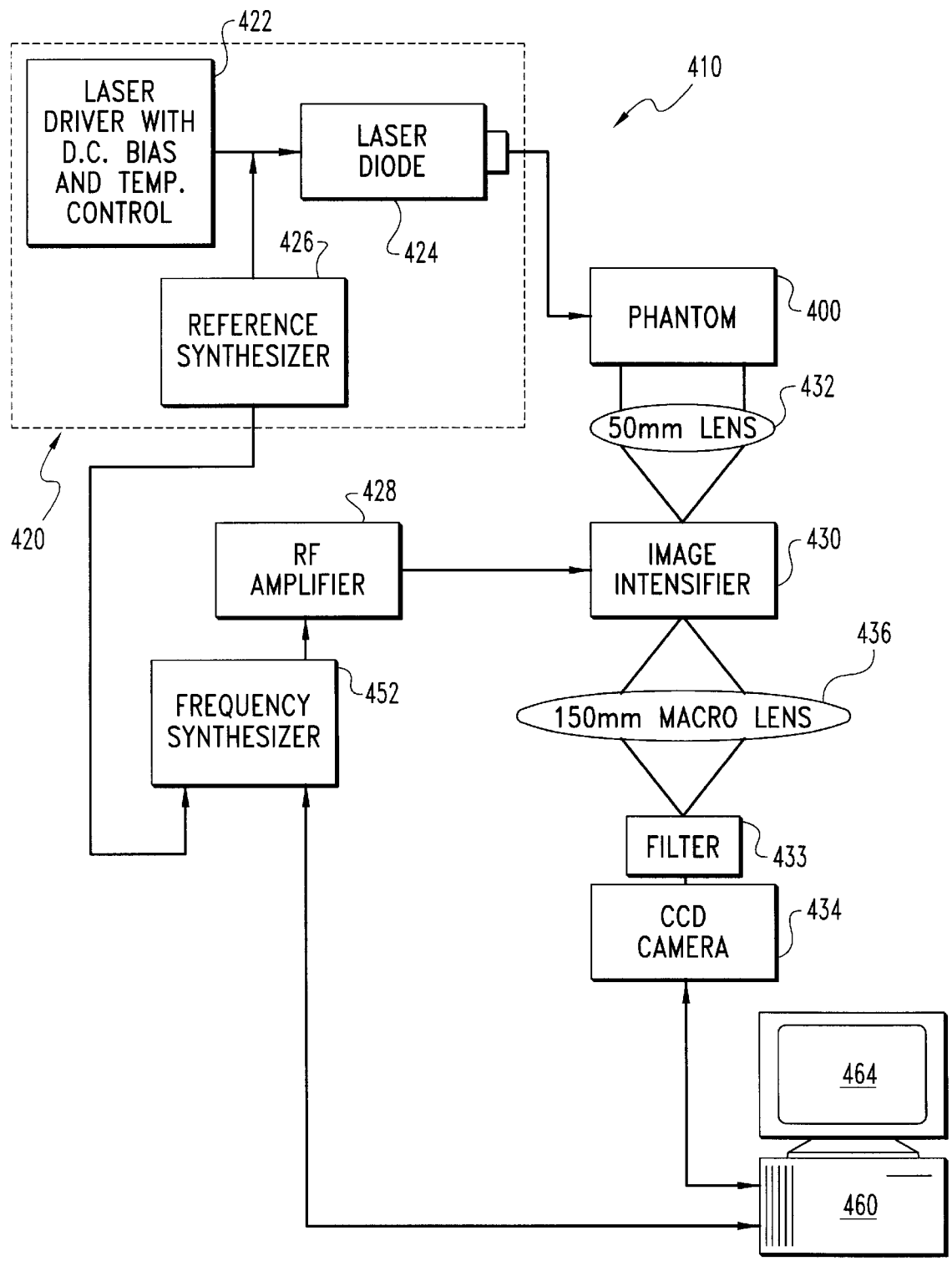
FIG. 15 is a schematic illustration of a system of an alternative embodiment of the present invention.

FIG. 15 depicts an optical system 410 of another embodiment of the present invention. This system includes modulated light source 420 with laser driver 422, operatively coupled laser diode 424, and reference frequency generator 426. Source 420 is configured to deliver modulated light to tissue phantom 400, and the re-emitted light from the phantom is focused onto a gain modulated image intensifier 430 via 50 mm lens 432. Intensifier 430 includes a photocathode face which converts photons to electrons, a Multi-Channel Plate (MCP) which multiplies the electronic signal by avalanche multiplication, and a phosphorescent screen which converts electrons into an optical image. Preferably, intensifier 430 is a fast intensifier, of the variety manufactured by Litton Electronics, Inc., which enables modulation by applying a DC bias and an RF signal from amplifier 428 between the photocathode and the MCP. For this example, the modulation of the image from intensifier 430 is phase-locked to the laser diode 424 by a 10 MHz output signal from synthesizer 426. By modulating the laser diode 424 and the image intensifier 430 at the same frequency, a steady-state image results on the phosphor screen. U.S. Pat. No. 5,213,105 to Gratton et al. provides additional background concerning certain aspects of this technique. The image from the phosphor screen is focused through interference filter 433 on a Charge Coupled Device (CCD) camera 434 via 150 mm macro lens 436. Camera 434 has a 512×512 array of CCD detectors configured to provide a corresponding pixelated image. Camera 434 is operatively coupled to processor 460 of a similar configuration to processor 160 previously described.

Following each acquired image, a phase delay between the image intensifier 430 and the laser diode 424 is induced by stepping the phase of the image intensifier 430 to values between 0 and 360 degrees with the frequency synthesizer 452 under the control of processor 460. Since the gain modulation of image intensifier 430 and laser diode 424 occurs at the same frequency, homodyning results in a steady phosphorescent image on intensifier 430 which is dependent upon phase. Preferably, control between synthesizer 452 and processor 460 is obtained by a conventional GPIB interface. Images from the phosphorescent screen of the image intensifier 430 are then gathered at each phase delay. The incremental phase delayed images are then used to generate a map of phase-shift and intensity modulation ratio between the excitation and re-emitted light from phantom 400. By applying interference or appropriate optical filters, the emission light may be selectively separated from the excitation light and measured. Camera 434 output may be processed by processor 460 using process 210.

The present invention will be further described with reference to the following specific examples 1–3. It will be understood that these examples are illustrative and not restrictive in nature. Examples 1–3 involve the computer simulation of the process 210. Simulations of this kind, including the simulation of tissue, are an acceptable means of demonstrating fluorescent spectroscopic imaging performance to those skilled in the art. The examples use simulated values obtained by solving the diffusion equations (1) and (2) for $\theta_m$ and $M_m$ under the conditions of table 2 as follows:

TABLE 2

| Case | $\mu_{a_{x \to m}}$ (mm$^{-1}$) | $\mu_{a_m}$ (mm$^{-1}$) | $\mu_{s_x}$ or $\mu_{s_m}$ (mm$^{-1}$) | $\tau$ (background) (ns) | $\eta\mu_{a_{x \to m}}$ (background) (mm$^{-1}$) | Gaussian Noise in log of AC intensity $\sigma_M$ | Gaussian Noise in phase $\sigma_\theta$ (degrees) |
|---|---|---|---|---|---|---|---|
| 5.1 | 0.0 | 0.0 | 1.0 | 10.0 | $1.0 \times 10^{-5}$ | 0.01 | 0.1 |
| 5.2 | $1.0 \times 10^{-3}$ | 0.0 | 1.0 | 10.0 | $1.0 \times 10^{-5}$ | 0.01 | 0.1 |
| 5.3 | 0.0 | 0.0 | 1.0 | 10.0 | $1.0 \times 10^{-5}$ | 0.01 | 1.0 |

The examples simulate tissue phantom 300 of FIG. 3 having a 100 mm diameter. Values of $\theta_m$ and $M_m$ were computed at each of the D1–D20 detection sites of FIG. 3 in response to the 4 modulated light sources S1–S4 located at the periphery. The excitation light modulation frequency f was simulated at 150 MHz. Diffusion equations (1) and (2) were solved to provide 80 simulated values of $\theta_m$ and $M_m$ corresponding to the various combinations of detection and source sites (Sk*Di=4×20=80). Gaussian noise with a standard deviation of 0.1 degrees (or a liberal 1 degree) in $\theta_m$ and 1% in $M_m$ were superimposed on the diffusion equation solutions. Adapted MUDPACK routines were used to solve the diffusion equations (1) and (2) on a SunSparc10 computer. These obtained data sets were used as simulated input data to process 210 for examples 1–3. The results are shown in tables 3 and 4 are as follows:

TABLE 3

| Case | Area, object 1 (mm$^2$) | Location, object 1 (x,y), (mm, mm) | Area, object 2 (mm$^2$) | Location, object 2 (x,y), (mm, mm) |
|---|---|---|---|---|
| 5.1 | 706.0 (expected) 742.2 (obtained) | (60,60) (expected) (60.8,58.5) (obtained) | not applicable | not applicable |
| 5.2 | 706.0 (expected) 703.1 (obtained) | (60,60) (expected) (59.4,58.3) (obtained) | not applicable | not applicable |
| 5.3 | 314.1 (expected) 381.0 (obtained) | (32.3,67.7) (expected) (34.0,67.7) (obtained) | 314.1 (expected) 342.0 (obtained) | (67.7,32.3) (expected) (65.0;35.0) (obtained) |

TABLE 4

| Case | $\eta\mu_{ax \to m}$ (object) (mm$^{-1}$) | $\tau$ (object) (ns) |
|---|---|---|
| 5.1 | $1.0 \times 10^{-3}$ (expected) $0.93 \times 10^{-3}$ (obtained) | 1.0 (expected) 1.03 (obtained) |
| 5.2 | $1.0 \times 10^{-3}$ (expected) $0.8 \times 10^{-3}$ (obtained) | 1.0 (expected) 0.7 (obtained) |
| 5.3 | (top left object): $1.0 \times 10^{-3}$ (expected) $2 \times 10^{-3}$ (obtained) (bottom right object): $2.0 \times 10^{-3}$ (expected) $1.8 \times 10^{-3}$ (obtained) | (top left object): 1.0 (expected) 4.1 (obtained) (bottom right object): 2.0 (expected) 3.5 (obtained) |

EXAMPLE 1

Figure 8:
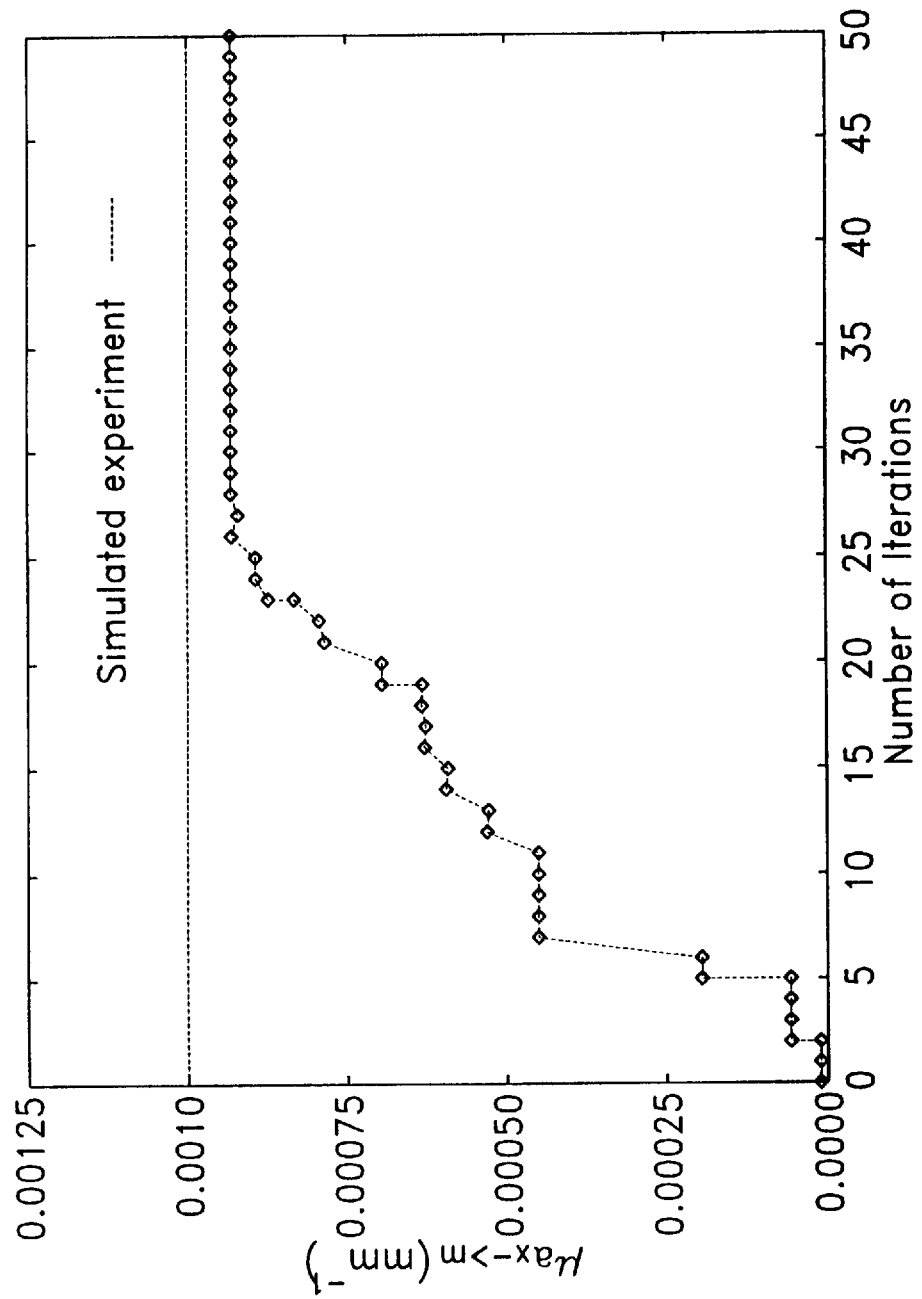
FIGS. 8 and 9 graphically depict convergence of simulated determinations of the spatial variation of fluorescent yield and lifetime, respectively, utilizing one embodiment of the present invention.
Figure 9:
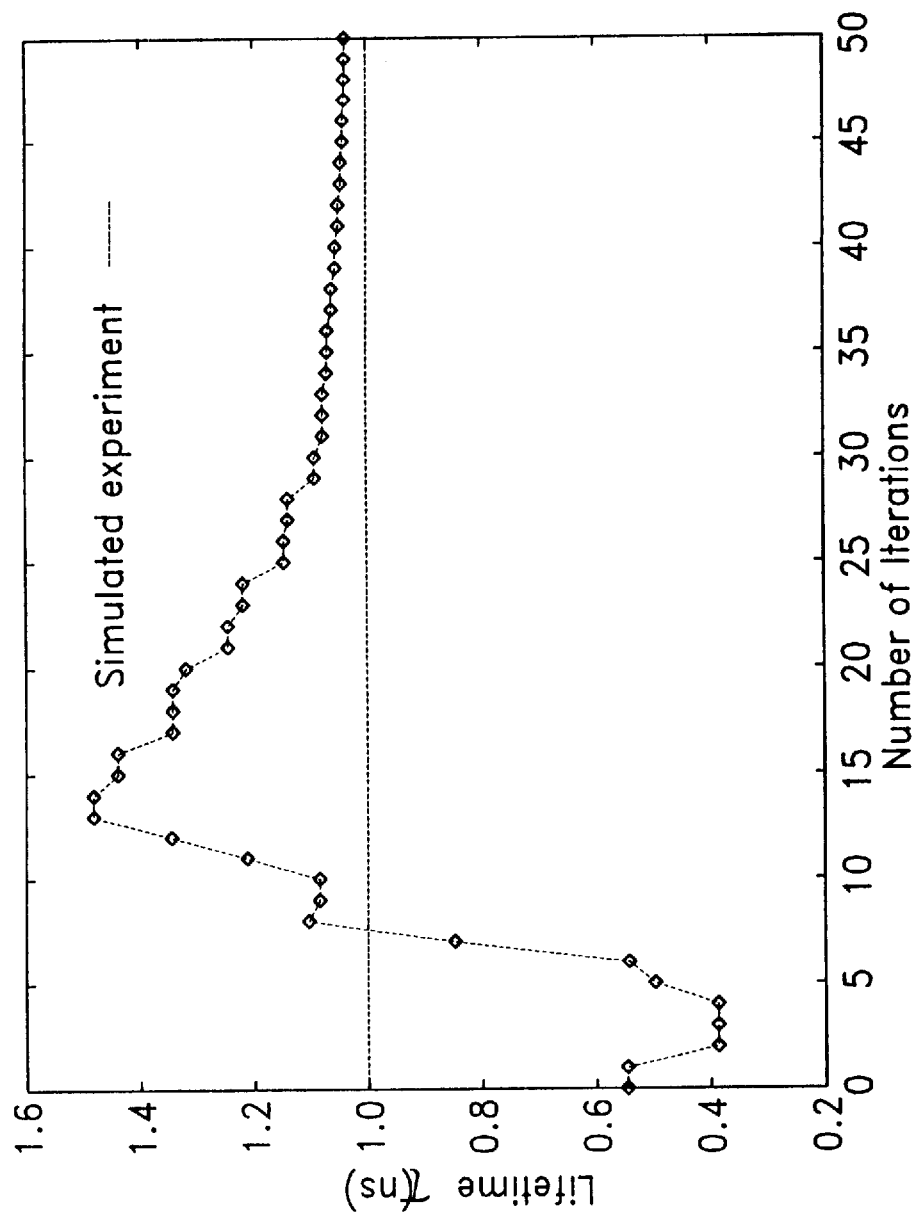
Figure 10:
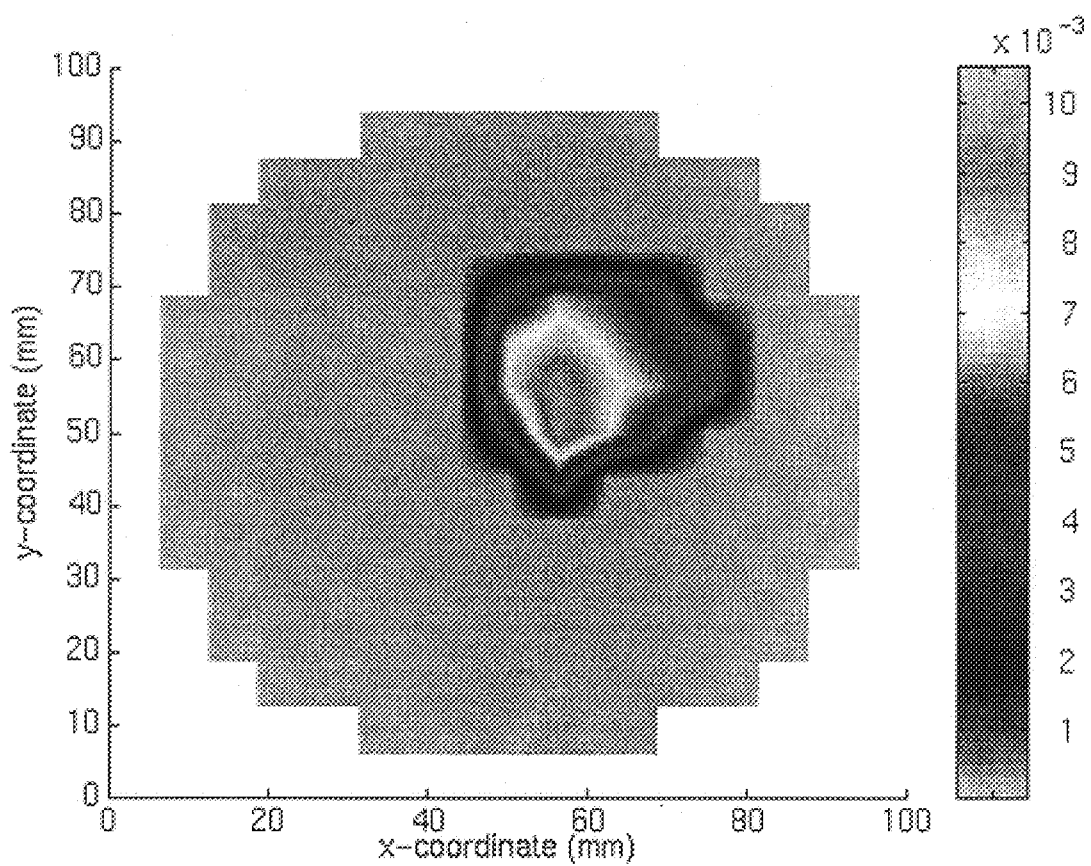
FIGS. 10–14 are images obtained from experimental examples 1–3 of the present invention.
Figure 11:
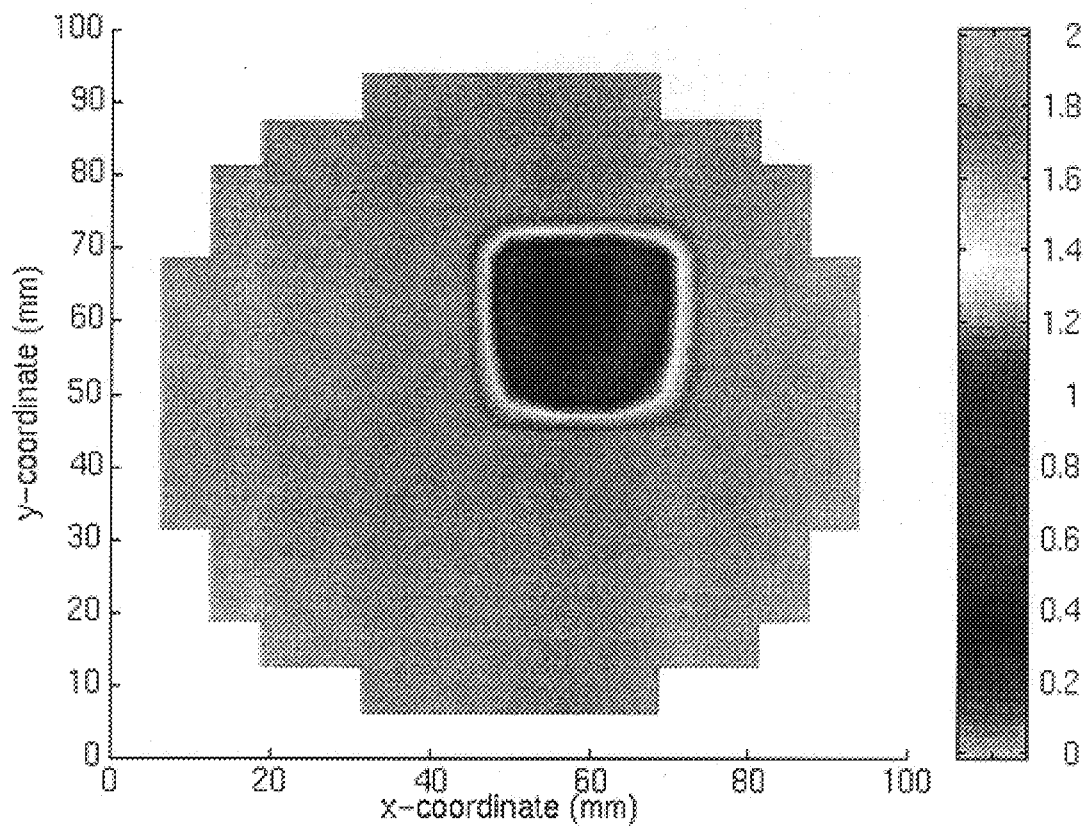

Example 1 reconstructs fluorescent yield and lifetime with no absorption due to non-fluorescing chromophores. To simulate the experimental data for this example, the fluorescent yield, $(\eta\mu_{a_{x \to m}})_j$, for the background and the heterogeneity 302 were chosen as $1 \times 10^{-5}$ mm$^{-1}$ and $1 \times 10^{-3}$ mm$^{-1}$ respectively and the fluorescence lifetime, $(\tau)_j$, for the background and the heterogeneity 302 chosen as 10 ns and 1 ns respectively. During the execution of loop 220, no a priori knowledge of either the heterogeneity 302 location or the background fluorescence properties was assumed and a uniform guess of $1 \times 10^{-5}$ mm$^{-1}$ and 10 ns was given for the fluorescence yield, $(\eta\mu_{a_{x \to m}})_j$, and lifetime, $(\tau)j$, respectively. Convergence was achieved in less than 50 iterations of Loop 220 (computational time on a SunSparc10: 2 hours) for a two dimensional 17×17 grid. The average values of $\eta\mu_{a_{x \to m}}$ and $\tau$ in the grid points which occupy the simulated object converge within 50 iterations to $\eta\mu_{a_{x \to m}} = 0.93 \times 10^{-3}$ mm$^{-1}$ and $\tau = 1.03$ ns are illustrated in FIGS. 8 and 9, respectively. FIGS. 10 and 11 illustrate the reconstructed images from the mapped values of $\eta\mu_{a_{x \to m}}$ and $\tau$, respectively, and are representative of the expected images. The images were smoothed by interpolation in examples 1–3 to remove spurious points which had unphysically high values, but were surround by values within a physically achievable range. These spurious values were replaced by the average background fluorescence yield and lifetime obtained from simulation of loop 220.

The average values of $\eta\mu_{a_{x \to m}}$ in the grid points which occupy the simulated background converge within 50 iterations to $9 \times 10^{-5}$ mm$^{-1}$. The value of the background converges to 5.4 ns. The dependence of the final images on the choice of the initial guess was examined by providing an initial uniform guess of $1 \times 10^{-4}$ mm$^{-1}$ and 10 ns for $(\eta\mu_{a_{x \to m}})_j$, and lifetime, $(\tau)_j$, respectively. This resulted in similar images to those obtained in FIGS. 10 and 11.

The location of heterogeneity 302 was identified as consisting of all the grid points with $\eta\mu_{a_{x \to m}}$ higher than 35% (arbitrarily chosen) of the peak value of the $\eta\mu_{a_{x \to m}}$ (FIG. 10). The average of the coordinates of all the identified object grid points was the position (60.8, 58.5) which is close to position (60, 60) that was used to simulate the experimental data. As listed in Table 3, the area of the heterogeneity based upon our arbitrary definition for identification was 72 mm$^2$, close to that used to generate our simulated experimental data.

EXAMPLE 2

Figure 12:
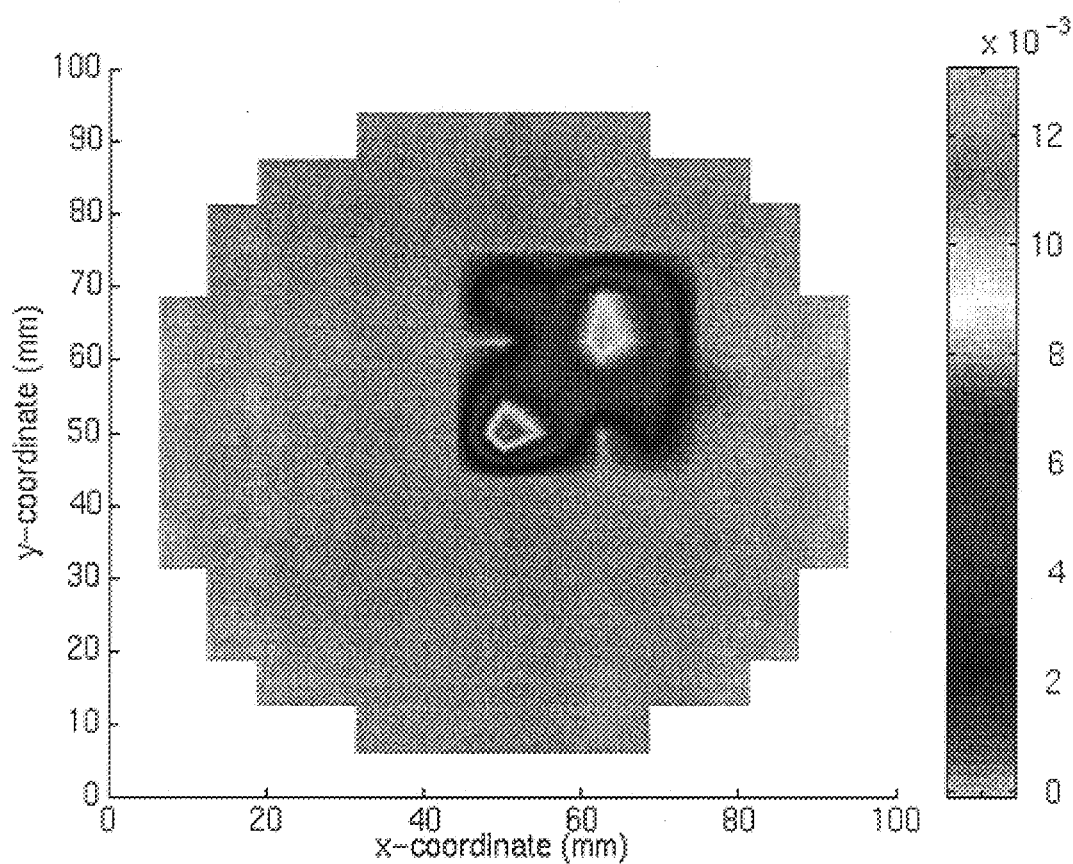
Figure 13:
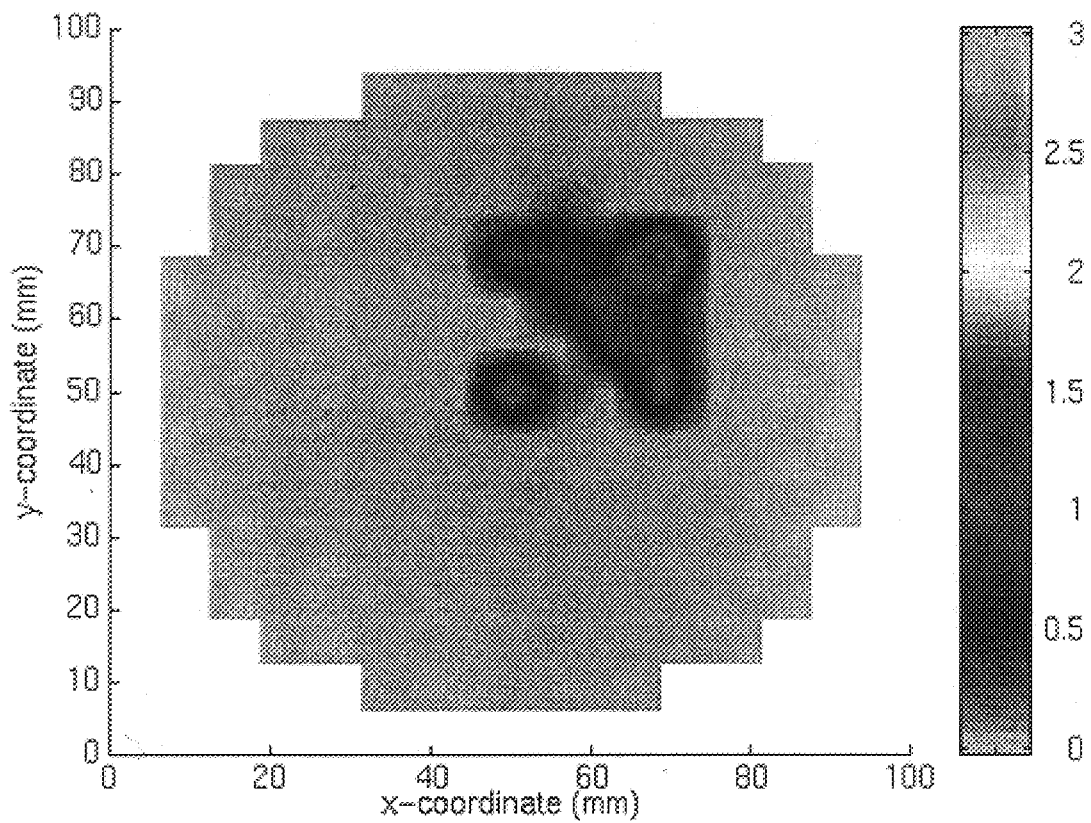

Example 2 reconstructs fluorescent yield and lifetime with a simulated chromophore absorption configured to mimic tissue. The same hidden heterogeneity as well as optical parameters and simulation equipment were used as described in Example 1 except that a uniform background chromophore absorption coefficient, $\mu_{a_{x,r}}$ of $1 \times 10^{-3}$ mm$^{-1}$ was used to generate the simulated experimental data. While excitation light propagation was not employed for image reconstruction, we considered this optical property known to estimate the best possible performance for inverse image reconstruction under physiological conditions. The two-dimensional reconstructed spatial map of the fluorescence yield, $(\eta\mu_{a_{x \to m}})_j$, and lifetime, $(\tau)_j$, are shown in FIGS. 12 and 13, respectively. As shown in Table 3, the mean value of location of the object according to our criterion based on $\eta\mu_{a_{x \to m}}$ occurred as position (59.4, 58.3) consistent with the conditions used to simulate the experimental data. The dimension of the heterogeneity based upon our arbitrary definition for identification (all grid points with $\eta\mu_{a_{x \to m}}$ higher than 35% of the maximum) were 703 mm$^2$ which is close to that used to generate our simulated experimental data. The average values of $\eta\mu_{a_{x \to m}}$ and $\tau$ in the grid points which occupy the simulated object converge within 50 iterations to the values of $\eta\mu_{a_{x \to m}}=0.8 \times 10^{-3}$ mm$^{-1}$ and $\tau=0.7$ ns consistent with the values used to generate the simulated experimental data (see Table 3). The average values of $\eta\mu_{a_{x \to m}}$ and $\tau$ in the grid points which occupy the simulated background converge within 50 iterations to values similar to that reported for Example 1.

EXAMPLE 3

Figure 14:
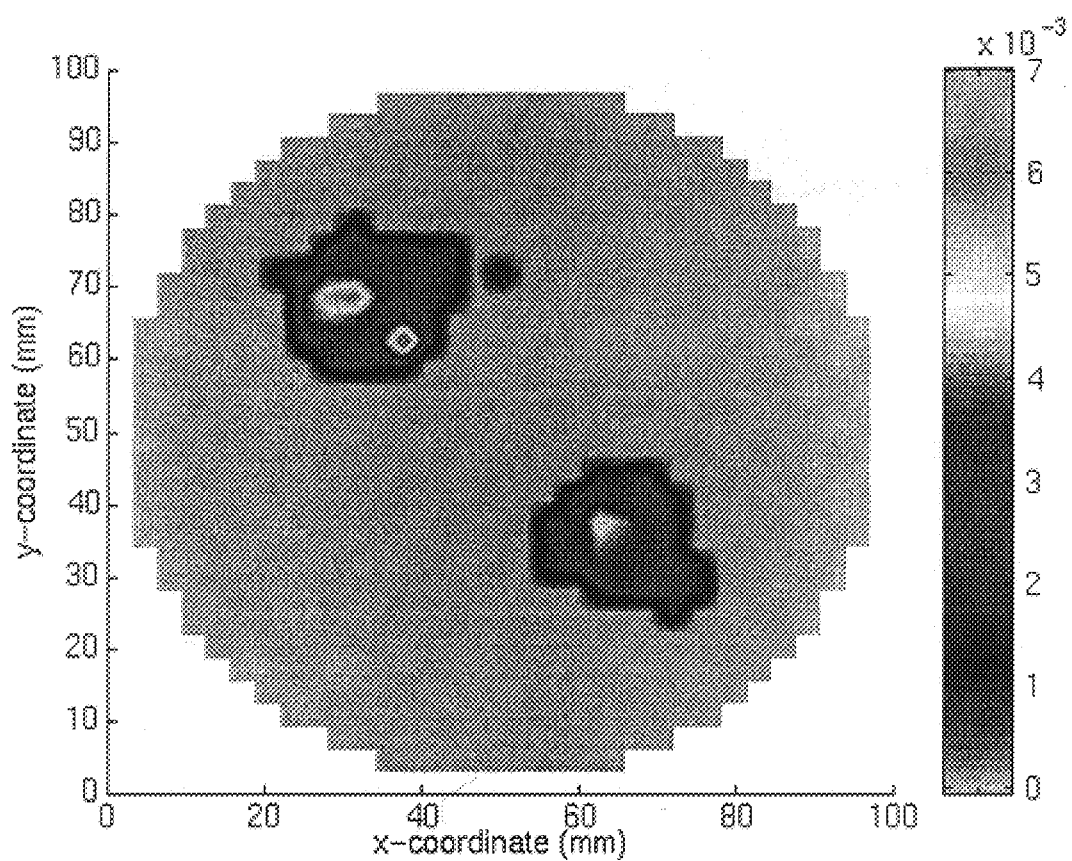

Example 3 simulated two hidden heterogeneities in the tissue phantom (not shown in FIG. 3). In this case, the same optical parameters were used as described in example 1 except that the fluorescence yield $\eta\mu_{a_{x \to m}}$ for the objects 1 and 2 was chosen as $1 \times 10^{-3}$ mm$^{-1}$ and $2 \times 10^{-3}$ mm$^{-1}$ respectively and lifetime $\tau$ for the heterogeneities chosen as 1 ns and 2 ns, respectively. A 33×33 grid was employed instead of a 17×17 grid. An image corresponding to the mapping of yield is depicted in FIG. 14.

All publications and patent applications cited in this specification are herein incorporated by reference as if each individual publication or patent application were specifically and individually indicated to be incorporated by reference. While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of imaging, comprising the steps of:
    (a) exposing a surface of a light scattering material to an excitation light from a light source, the material having a heterogeneous composition under the surface;
    (b) detecting a fluorescent emission from the material in response to step (a);
    (c) establishing an estimate of spatial variation of a fluorescence characteristic of the material;
    (d) determining a calculated emission as a function of the estimate;
    (e) comparing the calculated emission to the emission detected in step (b) to determine an error;
    (f) providing a modified estimate of spatial variation of the fluorescence characteristic and repeating steps (d) through (f) until the error reaches a desired minimum; and
    (g) generating an image of the material from the modified estimate, the image corresponding to the heterogeneous composition of the material.

2. The method of claim 1, further comprising introducing a fluorescent contrast agent into the material.

3. The method of claim 1, wherein step (f) includes applying a Jacobian matrix.

4. The method of claim 1, wherein the expected emission is determined as a function of a diffusion equation.

5. The method of claim 1, wherein step (e) includes comparing intensity and phase of the calculated emission to intensity and phase of the emission detected in step (b).

6. The method of claim 1, wherein the material includes a fluorescent contrast agent and the fluorescence characteristic is a function of at least one of fluorescence quantum efficiency, fluorescence lifetime, and concentration of the fluorescent contrast agent.

7. The method of claim 6, wherein the fluorescence characteristic is a function of fluorescence quantum efficiency, the light source is intensity modulated at a predetermined frequency, step (e) includes comparing AC intensity and phase of the calculated emission to intensity and phase of the emission detected in step (b), step (f) includes applying a Jacobian operator, and the expected emission is determined as a function of a photon fluence rate within the tissue.

8. A system for imaging a light scattering tissue having a heterogeneous composition and containing a fluorophore, comprising:
    (a) a light source with a pre-determined time varying intensity, said source being adapted to excite the fluorophore;
    (b) a sensor configured to provide a detected light signal corresponding to a multiply scattered light emission from the tissue in response to light from said source;
    (c) a processor operatively coupled to said sensor and responsive to said detected light signal to provide a number of values representative of a level of a fluorescence characteristic of the tissue as a function of position, the level of the fluorescence characteristic varying with the heterogeneous composition of the tissue and corresponding to at least one of fluorescence lifetime, fluorescence quantum efficiency, fluorescence yield, and fluorophore uptake, said processor being configured to generate an image signal as a function of said values; and
    (d) an output device responsive to said image signal to provide an image corresponding to the heterogeneous composition of the tissue.

9. The system of claim 8, further comprising a number of modulated light sources.

10. The system of claim 8 wherein said fluorescence characteristic corresponds to fluorescence yield.

11. The system of claim 8, wherein said sensor is configured to detect said emission at a number of locations along a surface of the tissue.

12. The system of claim 8, wherein said processor is configured to determine said values from a comparison of a calculated emission to an observed emission derived from said detected light signal, said calculated emission being determined as a function of an estimated spatial variation of said fluorescence characteristic, said estimated variation being updated and said comparison being repeated until a difference between said calculated emission and said observed emission reaches a desired minimum.

13. The system of claim 8, wherein said source includes a laser diode and said sensor includes a CCD camera.

14. The system of claim 8, wherein:
    said processor determines said values from an equation modeling diffusion of multiply scattered light through the tissue; and said predetermined time-varying intensity of said light source includes intensity modulation of said light source at a predetermined frequency; and said fluorescence characteristic is determined by said processor from at least one of a measured amplitude or a measured phase shift of said light emission.

15. A method of tissue analysis, comprising:
(a) exposing a biologic tissue to an excitation light with a pre-determined time varying intensity, the tissue multiply scattering the excitation light;
(b) detecting a multiply scattered light emission from the tissue in response to said exposing;
(c) determining a number of values from the emission with a processor, the values each corresponding to a level of a fluorescence characteristic at a different position within the tissue, the level of the characteristic varying with tissue composition; and
(d) generating an image of tissue compositional variation in accordance with the values.

16. The method of claim 15, wherein the fluorescence characteristic corresponds to at least one of fluorescence lifetime, fluorescence quantum efficiency, fluorescence yield, and fluorophore uptake.

17. The method of claim 15, further comprising introducing an exogenous fluorophore into the tissue.

18. The method of claim 15, wherein the fluorescence characteristic is independent of the intensity of thee emission.

19. The method of claim 15, wherein the fluorescence characteristic is independent of fluorophore concentration.

20. The method of claim 15, wherein the fluorescence characteristic varies with a metabolic property of the tissue.

21. The method of claim 15, wherein said determining includes (i) establishing an estimate of the values, (ii) providing a calculated emission as a function of the estimate, (iii) comparing the calculated emission to the emission of said detecting to determine an error, and (iv) providing a modified estimate of the fluorescence characteristic as a function of the error.

22. The method of claim 15 wherein said exposing includes exciting the tissue with a time-varying light source at a number of different frequencies, and the values are determined as a function of the different frequencies.

23. The method of claim 15, wherein said determining includes determining the values from a mathematical relationship modeling multiple light scattering behavior of the tissue.

24. The method of claim 23, wherein the relationship corresponds to a diffusion equation approximation of multiply scattered light.

25. The method of claim 23, wherein said excitation light is intensity modulated at a predetermined frequency, and said determining includes establishing at least one of a measured amplitude or a measured phase shift of the emission relative to the excitation light.

26. A method of tissue analysis, comprising:
(a) introducing an fluorescent agent into a light scattering biologic tissue with a heterogeneous composition;
(b) exposing the tissue to light from a light source with a pre-determined time varying intensity to excite the agent, the tissue multiply scattering the excitation light;
(c) detecting a multiply scattered light emission from the tissue in response to said exposing;
(d) quantitizing a fluorescence characteristic throughout the tissue from the emission by establishing a number of values with a processor, the values each corresponding to a level of the fluorescence characteristic at a different position within the tissue, the level of the fluorescence characteristic varying with heterogeneous composition of the tissue; and
(e) mapping the heterogeneous composition of the tissue in accordance with the values.

27. The method of claim 26, wherein the fluorescence characteristic corresponds to uptake of the agent and further comprising mapping a number of quantities corresponding to adsorption and scattering coefficients of the tissue before said introducing.

28. The method of claim 26, wherein the fluorescence characteristic corresponds to at least one of fluorescence lifetime, fluorescence quantum efficiency, fluorescence yield and fluorophore uptake.

29. The method of claim 26, wherein the fluorescence characteristic is independent of the intensity of the emission.

30. The method of claim 26, wherein the fluorescence characteristic is independent of fluorophore concentration.

31. The method of claim 26, wherein said quantizing includes (i) establishing an estimate of the values, (ii) determining a calculated emission as a function of the estimate, (iii) comparing the calculated emission to the emission of said detecting to determine an error, (iv) providing a modified estimate of the fluorescence characteristic as a function of the error.

32. The method of claim 26, wherein said quantitizing includes determining the values from a mathematical relationship modeling multiple light scattering behavior of the tissue.

33. The method of claim 32, wherein the relationship corresponds to a diffusion equation approximation of multiply scattered light.

34. The method of claim 26, further comprising monitoring a metabolic property of the tissue in vivo by detecting variation of the fluorescence characteristic.

35. A method of tissue analysis, comprising:
(a) establishing a first set of values corresponding to adsorption and scattering properties of a light scattering biologic tissue;
(b) introducing an fluorescent agent into the tissue after said establishing;
(c) establishing a second set of values corresponding to adsorption and scattering properties of the tissue after said introducing; and
(d) comparing the first set of values and the second set: of values to map uptake of the agent into the tissue.

36. The method of claim 35, further comprising mapping a fluorescence characteristic within the tissue corresponding to at least one of fluorescence lifetime, fluorescence quantum efficiency, and fluorescence yield.

37. The method of claim 35, wherein said establishing of said first set includes:
exposing the tissue to an intensity modulated excitation light from a light source, the tissue multiply scattering the excitation light; and
detecting a multiply scattered emission from the tissue in response to said exposing.

38. The method of claim 37, wherein said establishing of the first set includes (i) providing an estimate of the first set of values, (ii) determining a calculated emission as a function of the estimate, (iii) comparing the calculated emission to the emission of said detecting to determine an error, and (iv) providing a modified estimate of the first set of values as a function of the error.

39. The method of claim 35, wherein said establishing of said second set includes:

exposing the tissue to an intensity modulated excitation light from a light source, the tissue multiply scattering the excitation light; and detecting a multiply scattered emission from the tissue in response to said exposing.

40. The method of claim 35, wherein said establishing of the second set includes (i) providing an estimate of the second set of values, (ii) determining a calculated emission as a function of the estimate, (iii) comparing the calculated emission to the emission of said detecting to determine an error, and (iv) providing a modified estimate of the second set of values as a function of the error.

41. A system for imaging a light scattering tissue having a heterogeneous composition and containing a fluorophore, comprising:

(a) a means for exciting the fluorophore in the tissue;

(b) a means for detecting a light signal corresponding to a fluorescent emission from the tissue in response to said exciting means;

(c) a processor operatively coupled to said sensor and responsive to said light signal, said processor including a means for generating an output signal by iteratively estimating spatial distribution of a quantitized fluorescent characteristic of the tissue until a desired minimum error is obtained; and (d) a means for providing an image corresponding to the heterogeneous composition of the tissue in response to said output signal.

42. A method, comprising:

(a) exposing a biologic tissue with a hidden heterogeneity to an excitation light with a predetermined time-varying intensity, the tissue multiply scattering the excitation light;

(b) detecting a light emission from the tissue in response to said exposing; and (c) imaging the tissue to reveal the hidden heterogeniety by mapping spatial variation of a level of a fluorescence property of the tissue from the light emission in accordance with a mathematical relationship modeling multiple light scattering behavior of the tissue.

43. The method of claim 42, wherein the fluorescence property corresponds to at least one of fluorescence lifetime, fluorescence quantum efficiency, fluorescence yield, and fluorophore uptake.

44. The method of claim 42, wherein said exposing includes exciting the tissue with an intensity modulated light source it each of a number of different modulation frequencies, and the values are determined as a function of the different modulation frequencies.

45. The method of claim 42, further comprising:

(d) determining a first set of values corresponding to spatial variation of a fluorescence characteristic of the tissue;

(e) introducing a fluorescent agent into the tissue after said determining;

(f) establishing a second set of values corresponding to spatial variation of the fluorescence characteristic after said introducing; and (g) comparing the first set of values to the second set of values to map fluorophore uptake of the agent into the tissue, the fluorophore uptake being the fluorescence property.

46. The method of claim 42, wherein the fluorescence property characterizes a fluorophore residing in the tissue, the level of the fluorescence property is determined as a function of a number of time-based values corresponding to temporal transport of light through the tissue by multiple scattering, and the fluorescence property varies with chemical interaction of the fluorophore in the tissue.

47. The method of claim 46, wherein the fluorescence property is generally independent of fluorophore concentration.

* * * * *

UNITED STATES PATENT AND TRADEMARK OFFICE
CERTIFICATE OF CORRECTION

PATENT NO. : 5,865,754
DATED : February 2, 1999
INVENTOR(S) : Sevick-Muraca, et al.

It is certified that error appears in the above-identified patent and that said Letters Patent is hereby corrected as shown below:

Column 1,
Line 4, prior to "This" insert -- The U.S. government has a paid-up license in this invention and the right in limited circumstances to require the patent owner to license others on reasonable terms as provided for by the terms of NIH Award No. R01 CA61413, NIH Award No. R01 CA67176, and NIH Award No. K04 CA68374 awarded by the National Institute of Health. --

Signed and Sealed this

Sixth Day of November, 2001

Attest:

*Attesting Officer*

NICHOLAS P. GODICI
*Acting Director of the United States Patent and Trademark Office*